(12) United States Patent
Lam

(10) Patent No.: US 11,207,243 B2
(45) Date of Patent: Dec. 28, 2021

(54) SYSTEM, METHOD, AND MODULE FOR INTEGRATED MEDICATION MANAGEMENT

(71) Applicant: Bin Wai Lam, La Mesa, CA (US)

(72) Inventor: Bin Wai Lam, La Mesa, CA (US)

( * ) Notice: Subject to any disclaimer, the term of this patent is extended or adjusted under 35 U.S.C. 154(b) by 273 days.

(21) Appl. No.: 16/186,440

(22) Filed: Nov. 9, 2018

(65) Prior Publication Data

US 2019/0133888 A1 May 9, 2019

Related U.S. Application Data

(60) Provisional application No. 62/583,971, filed on Nov. 9, 2017.

(51) Int. Cl.
| | | |
|---|---|---|
| *A61J 7/04* | (2006.01) | |
| *G16H 20/13* | (2018.01) | |
| *G16H 10/60* | (2018.01) | |
| *A61J 1/03* | (2006.01) | |
| *A61J 7/00* | (2006.01) | |

(52) U.S. Cl.
CPC ............. *A61J 7/0481* (2013.01); *A61J 1/03* (2013.01); *A61J 7/0084* (2013.01); *A61J 7/049* (2015.05); *A61J 7/0418* (2015.05); *A61J 7/0445* (2015.05); *G16H 10/60* (2018.01); *G16H 20/13* (2018.01); *A61J 2200/30* (2013.01); *A61J 2200/70* (2013.01); *A61J 2205/10* (2013.01); *A61J 2205/30* (2013.01)

(58) Field of Classification Search
CPC ........ A61J 7/0481; A61J 7/0418; A61J 7/049; A61J 1/03; A61J 7/0445; A61J 7/0084; A61J 2200/30; A61J 2205/30; A61J 2205/10; A61J 2200/70; G16H 20/13; G16H 10/60
See application file for complete search history.

(56) References Cited

U.S. PATENT DOCUMENTS

| | | | | |
|---|---|---|---|---|
| 5,915,589 A | * | 6/1999 | Lim | A61J 7/0481 221/13 |
| 8,600,548 B2 | * | 12/2013 | Bossi | G16H 40/67 700/240 |
| 9,245,093 B2 | * | 1/2016 | Shaw | G16H 20/13 |

(Continued)

*Primary Examiner* — Michael Collins
(74) *Attorney, Agent, or Firm* — Innovation Capital Law Group, LLP; Vic Lin

(57) ABSTRACT

Systems, methods, and modules providing integrated medication management utilizing a medication management module. The module comprises cartridge slots, a pill extractor, a pill dispenser, and processors. The method includes receiving patient data of a patient, storing the patient data, and determining a presence of pill cartridges and pills. The module scans a cartridge label corresponding to the patient and the pills and authenticates the cartridges based on the patient data and the pills. The system determines, in response to authenticating, a medication regimen based on the patient data and pills and extracts pills from the pill cartridges. The module ensures verifying a correct extraction of pills and dispensing the pills at a predetermined time in a predetermined amount based on the medication plan. The module verifies a correct dispensing of pills at the predetermined time in the predetermined amount.

20 Claims, 15 Drawing Sheets

TOP VIEW (WITH DISC)

(56) References Cited

U.S. PATENT DOCUMENTS

| | | | |
|---|---|---|---|
| 2004/0158350 A1* | 8/2004 | Ostergaard | G16H 20/13 700/231 |
| 2005/0224510 A1* | 10/2005 | Remis | G16H 20/13 221/69 |
| 2006/0058724 A1* | 3/2006 | Handfield | A61J 7/0076 604/20 |
| 2007/0185615 A1* | 8/2007 | Bossi | G07F 17/0092 700/244 |
| 2008/0059228 A1* | 3/2008 | Bossi | G07F 17/0092 705/2 |
| 2008/0173711 A1* | 7/2008 | Handfield | G07F 9/026 235/385 |
| 2009/0281657 A1* | 11/2009 | Gak | G16H 20/13 700/242 |
| 2016/0354285 A1* | 12/2016 | Nolan | G06Q 10/109 |
| 2017/0326033 A1* | 11/2017 | Kraft | G16H 40/67 |

* cited by examiner

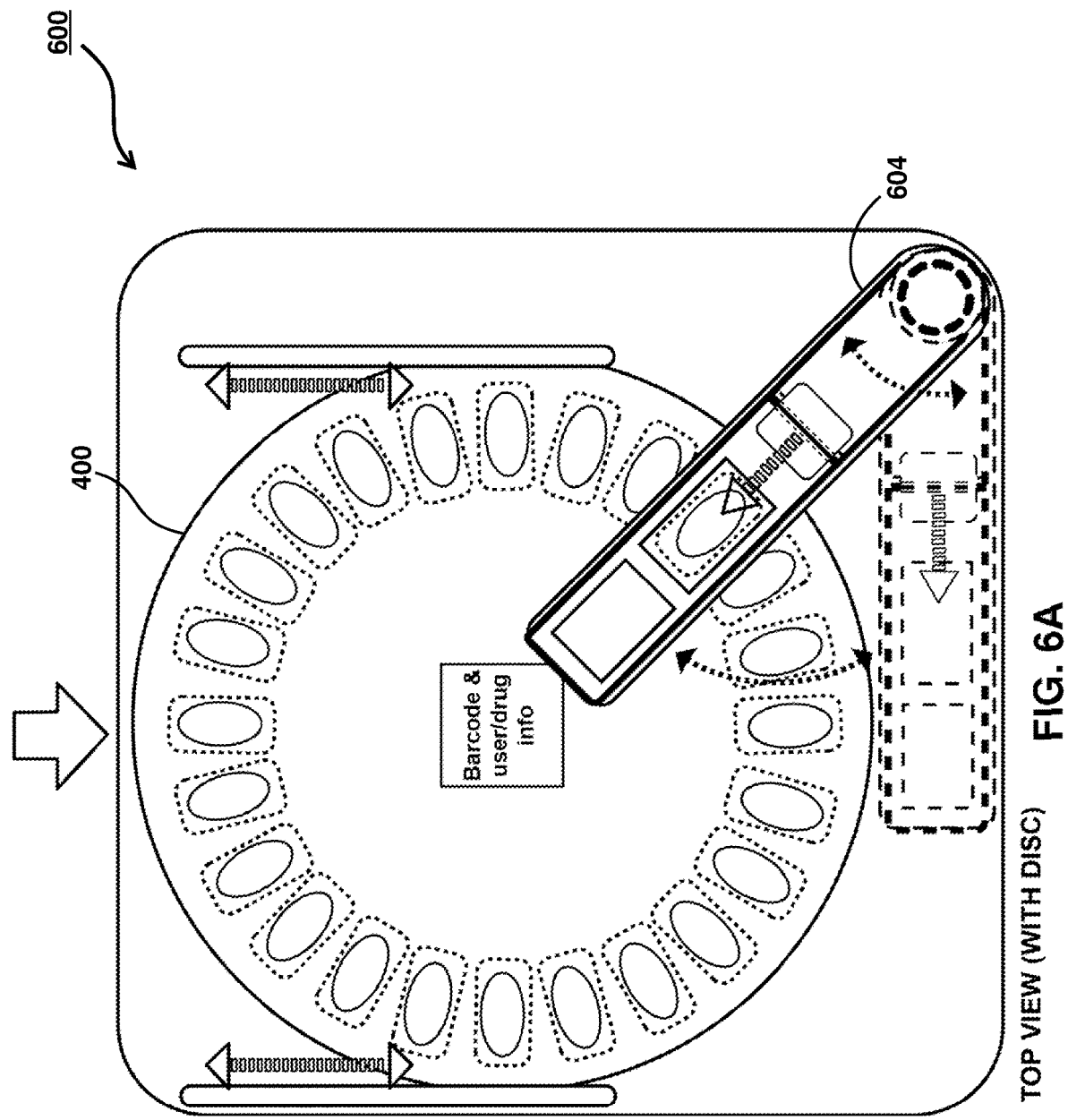

SYSTEM, METHOD, AND MODULE FOR INTEGRATED MEDICATION MANAGEMENT

CROSS-REFERENCE TO RELATED APPLICATIONS

This application claims priority under 35 U.S.C. § 119(e) from provisional U.S. patent application No. 62/583,971 filed on Nov. 9, 2017, the contents of which are expressly incorporated herein by reference.

BACKGROUND

1. Field

The present disclosure pertains to a system, method and module for integrated medication management.

2. Description of the Related Art

Automatic pill dispensers used for medication management are well known. Pill dispensers that have wireless connectivity are also well known. However, previous solutions directed to ensuring adherence and monitoring for non-compliance are inaccurate, costly and cumbersome.

SUMMARY

Accordingly, one or more aspects of the present disclosure relate to a method for integrated medication management for a patient, utilizing a medication management module comprising one or more cartridge slots, a pill extractor, a pill dispenser, and one or more processors. The processors are in communication with a memory having non-transitory machine-readable instructions stored thereon. When executed by the one or more processors the instructions configure the medication management module for receiving, by the one or more processors, patient data of a patient. The method includes storing, on the memory, the patient data, and determining a presence of one or more pill cartridges comprising one or more pills. The method determines, utilizing one or more cartridge slots; a cartridge label corresponding to the patient and the one or more pills. In one embodiment the method authenticates the one or more cartridges based on the patient data and the one or more pills and determines, in response to authenticating, a medication regimen based on the patient data and the one or more pills. The method may then extract the one or more pills from the one or more pill cartridges, verifying a correct extraction of the one or more pills. The method may dispense the one or more pills at a predetermined time in a predetermined amount based on the medication plan. The method includes verifying a correct dispensing of the one or more pills at the predetermined time in the predetermined amount.

One or more aspects of the present disclosure relate to an apparatus configured for providing integrated medication and care management, the apparatus comprises one or more cartridge slots configured to receive a pill cartridge comprising one or more pills. In some embodiments, the apparatus includes an extractor mechanism and one or more processors in communication with memory storing machine readable instructions thereon. In some embodiments, the one or more processors are configured to execute the machine-readable instruction. The machine-readable instructions cause the apparatus to receive, by the one or more processors, patient data of a patient and store, on the memory, the patient data. The apparatus may determine a presence of one or more pill cartridges (400) comprising one or more pills. In some embodiments, the apparatus determines, utilizing one or more cartridge slots, a cartridge label corresponding to the patient and the one or more pills. In some embodiments, the apparatus authenticates the one or more cartridges based on the patient data and the one or more pills. In some embodiments, the apparatus determines, in response to authenticating, a medication regimen based on the patient data and the one or more pills. In some embodiments, the apparatus includes extracting, utilizing the pill extractor, the one or more pills from the one or more pill cartridges and verifying a correct extraction of the one or more pills. In one embodiment, the apparatus dispenses the one or more pills at a predetermined time in a predetermined amount based on the medication regimen and verifies a correct dispensing of the one or more pills at the predetermined time in the predetermined amount.

One or more aspects of the present disclosure relate to a graphic user interface (147) comprising a display and a selection device and one or more processors in communication with memory storing machine readable instructions thereon, the one or more processor configured to execute the machine-readable instruction and cause the graphic user interface to: retrieving a set of pill options for the menu, each of the pill options representing a medication regimen of a patient, displaying the set of pill options of the patient on the display, receiving a menu entry selection signal indicative of the selection device pointing at a selected pill option from the set of pill options; and in response to the signal, performing a search of a real time available pharmacist based on the pill option selection displaying a real time video feed on the user interface corresponding to the real time available pharmacist.

One or more aspects of the present disclosure relate to a pill cartridge configured for use in a medication management module comprising an extractor mechanism. The pill cartridge comprising one or more pill pockets configured to contain a pill, a label, a patient ID, a pill ID, one or more spindle apertures configured to physically engage the extractor mechanism, wherein the pill cartridge is configured for error-proof insertion into the medication management module.

One or more aspects of the present disclosure relate to an extractor mechanism configured for use in a medication management module to extract a pill from a pill cartridge. The extractor mechanism comprising a pill extractor configured to extract the pill from the pill cartridge at least one of an optic sensor, a camera, or a motor; a pill chute, at least one spindle finger configured to physically engage the pill cartridge. Wherein the at least one of the optic sensor, the camera, or the motor are configured to verify the correct extraction of the pill through the pill chute. One or more spindle apertures configured to physically engage the extractor mechanism; wherein the pill cartridge is configured for error-proof insertion into the medication management module. These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

FIG. 6A-6B is a schematic representation of a pill extractor in accordance with one or more embodiments;

DETAILED DESCRIPTION OF EXEMPLARY EMBODIMENTS

Figure 1:
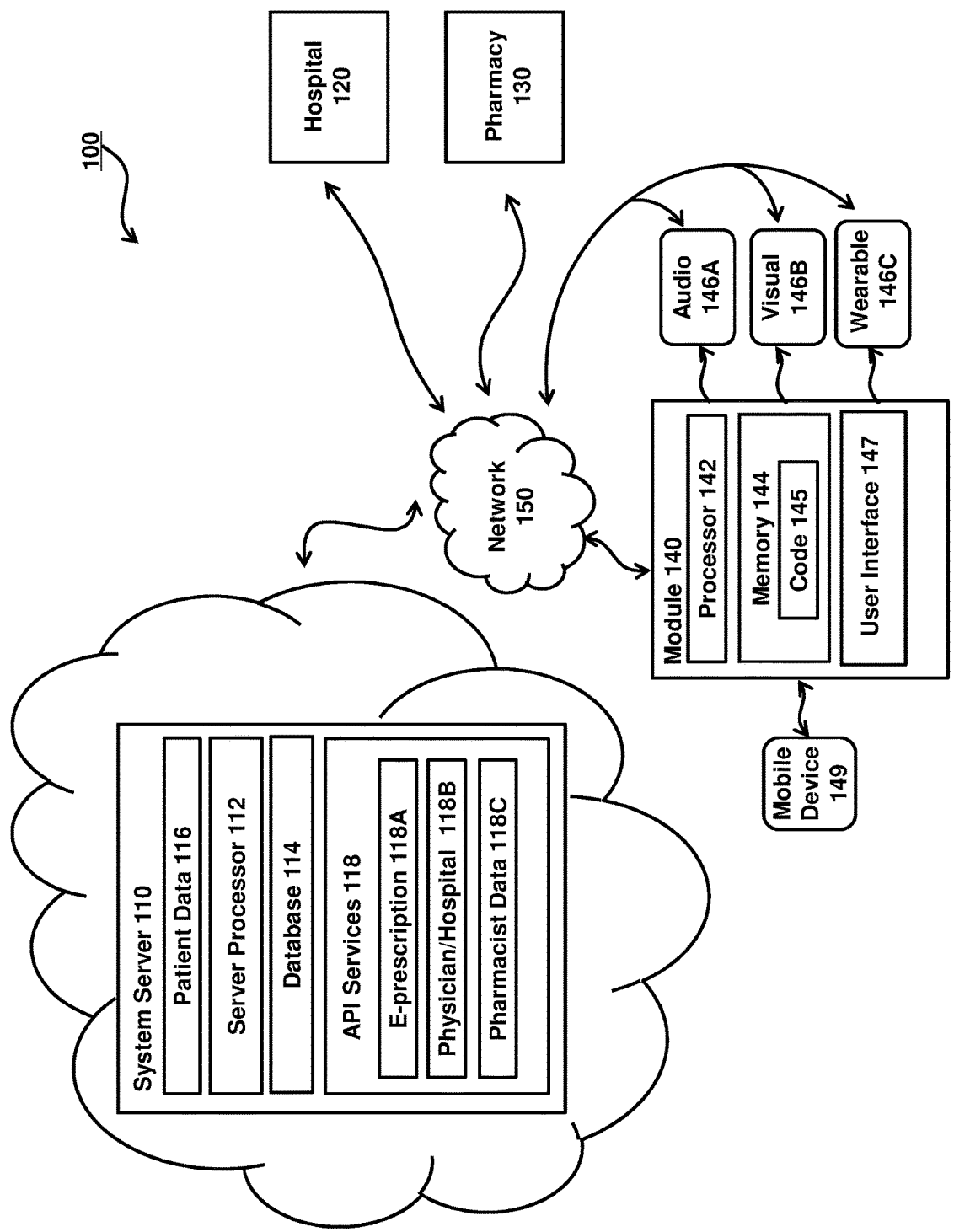
FIG. 1 is a schematic representation of a system for integrated medication management in accordance with one or more embodiments.

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements.

Moreover, where certain elements of the present invention can be partially or fully implemented using known components, only those portions of such known components that are necessary for an understanding of the present invention will be described, and detailed descriptions of other portions of such known components will be omitted so as not to obscure the invention. As used herein, the singular form of "a", "an", and "the" include plural references unless the context clearly dictates otherwise. As used herein, the statement that two or more parts or components are "coupled" shall mean that the parts are joined or operate together either directly or indirectly (i.e., through one or more intermediate parts or components, so long as a link occurs).

Embodiments described as being implemented in hardware should not be limited thereto, but can include embodiments implemented in software, or combinations of software and hardware, and vice-versa, as will be apparent to those skilled in the art, unless otherwise specified herein. In the exemplary embodiments described herein, an embodiment showing a singular component should not be considered limiting; rather, the invention is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

As used herein, "directly coupled" means that two elements are directly in contact with each other. As used herein, "fixedly coupled" or "fixed" means that two components are coupled so as to move as one while maintaining a constant orientation relative to each other. As used herein, "operatively coupled" means that two elements are coupled in such a way that the two elements function together. It is to be understood that two elements "operatively coupled" does not require a direct connection or a permanent connection between them.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality). Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

It should be noted that, while one or more operations are described herein as being performed by particular components of system 100, those operations may, in some embodiments, be performed by other components of system 100. As an example, while one or more operations are described herein as being performed by components of medication management module 110 processor 141, those operations may, in other embodiments, be performed by components of the mobile device(s) 148, by components of the system sever 110, and/or by other components of system 100.

In the United States alone, medication and care plan non-compliance leads to 125,000 preventable deaths annually. And nearly 200,000 preventable hospitalizations of older adults annually in the US alone. This causes to $290 billion in avoidable medical spending. While some companies and solutions have tackled medication non-compliance and adherence problems, most solutions merely focus on reminding patients to take their medication and/or informing caregivers of missed dosages. While some existing solutions may meet the needs of certain patients by reminding when to take medication, existing solutions do not address compliance issues while eliminating the potential for human error. For example, some solutions that provide reminders lack functionality to eliminate the potential for sorting errors. Moreover, existing solutions do not adequately leverage IoT (Internet of Things) functionality and ease of use to address aging-in-population.

With ever increasing aging-in-population, about 90% of seniors want to stay in their homes as they age according to organization such as AARP. However, many older adults may not be able to sort/organize their medication, particularly for those patients with cognition/physical challenges and are non-tech savvy. Currently, there are 45-65 million of unpaid family caregivers in the United States alone. Projections indicate that by 2020, 117 million Americans will need caregiving assistance. Dealing with tremendous burden and stress, emotionally, physically and financially, many of these unpaid caregivers are "sandwich" generation—taking care of both elderly parents and children. One of the most onerous and time-consuming tasks for caregivers is sorting and managing administration of multiple, ever-changing medications and medication plans. The risk of mismanagement where pills may be allocated, sorted, and/or administered incorrectly may lead to adverse side effects or even life threating circumstances. Accordingly, the exemplary embodiments described herein provide a simple, streamlined solution to mitigate the risk of medication mismanagement by users (e.g., patients and/or caregivers) and eliminating the potential for adverse health effects resulting from human-errors.

One or more exemplary implementations described herein provide a streamlined process, medication management module and medication packaging, such that users may simply leverage the 'Plug-&-Play' turnkey solution of the exemplary embodiments described herein, without the hassle of going to a retail Pharmacy to pick up medicine, organize them in a pillbox or dispenser, and repeating the typical gauntlet indefinitely. The exemplary embodiments described herein provide the ability for users to provide the highest accuracy and medication management so they may focus their time and energy on themselves.

Accordingly, one or more embodiments described herein may provide methods, systems, and modules for enabling users (patients and/or caregivers) to manage their medication safely and easily. Leveraging the "plug-and-play" technology described herein, users may organize and dispense medicines based on a medication plan with minimal energy and while completely eliminating the potential for repeated human-error. As used herein, users may include Caregivers, Care Recipients, Patients, or any person utilizing the medication management system described herein. As used herein medication or pills may reference any prescription medication/drugs, over the counter medicines, vitamins and/or other supplements. Medication/drugs/pills may, for example, include any size, color, and shape (tablet, capsule, lozenge, etc.).

One or more embodiments described herein provide a uniquely packaged pill cartridge configured for use in conjunction with pill management module providing a portable smart medicine dispenser for dispensing pills from the accompanied pill cartridge according to the scheduled regimen and also providing medication management functions as described in further detail below.

Referring now to FIG. 1, FIG. 1 depicts an exemplary system 100 for integrated medication and care management of a patient. In addition to dispensing medication based on a patient's regimen, the integrated medication and care management provided by exemplary system 100 includes further dynamic functionality to provide multiple care features. As discussed in further detail below, exemplary system 100 integrates features that encourage adherence and monitor non-compliance along with error proof pill dispensing functionality for ensuring adherence and non-compliance monitoring integrated into a convenient, cost effective and user friendly pill dispensing platform.

In some embodiments, exemplary system 100 may include system server 110, hospital 120, pharmacy 130, medication management module 140, and network 150. As shown in FIG. 1, system server 110, hospital 120, pharmacy 130, and medication management module 140. As used herein, hospital 120 may refer to any establishment that provides healthcare and issues prescription medications to patients. For example, hospital 120 may include a trauma center, and emergency room, a doctor's office, a dentist's office, payors, health plan insurers, and/or a mental health care facility such as a psychiatrist office. As used herein physicians may include clinics, nurses, and/or any other healthcare practitioner that prescribes prescription medication or should have access to exemplary system 100. As further used herein, pharmacy 130 may refer to an establishment that is licensed to fill and provide prescription medication to the public. Pharmacy 130 may also include pharmacists and other pharmacy professionals (e.g., technicians and Pharmacy Benefit Manager (PBM)).

In one embodiment, server 110, hospital 120, pharmacy 130 and medication management module 140 may all be in communication via network 150. For example, network 150 may include a LAN/WAN connection configured to provide an Internet connection via a hybrid fiber optic (HFC) transmission network, (e.g., Ethernet twisted shielded pair CAT-5, WiFi, premises coaxial cable network, or any other connection capable of establishing an Internet connection). In some embodiments, network 150 may include a wireless network capable of establishing an internet connection (e.g. 5G, LTE, 4G, CDMA, and the like).

For example, system server 110 may include server processors 112 in communication with database 114. Server processors 112 may communicate with hospital 120, pharmacy 130, and medication module 140 to send and receive commands and data related to patients, hospitals, pharmacies, drugs, and other medication management related information. Server processors 112 may receive data related to the medication regimen of the patient and store receive data as patient data 116 in database 114. Received data may include but is not limited to prescriptions issued by doctors treating the patient at hospital 120, information related to the patient's medication regimen received from pharmacy 130, and/or information related to the patient's medication regimen received from medication management module 140 (e.g., reporting non-compliance, requesting refills, real time request for link to pharmacist, which are discussed in further detail below).

For example, a patient (not shown) may be treated at hospital 120 to cure an ailment or disease. A doctor at hospital 120 may then prescribe the patient one or more prescriptions related to a care management plan. Discussed in further detail below, the care management plan may include but is not limited to: dietary restrictions, exercise/activity limitations, dosages/instructions of medication, and timing of dispensing such medications to the patient. Utilizing exemplary system 100, the doctor or hospital 120 may issue prescriptions, which are transmitted to system server 110 via network 150. System server 110 may store the prescription in database 124, for example as patient data 116 corresponding to a particular patient.

In some embodiments, database 114 may store patient data 116. Patient data 116 may include physical characteristics of the patient, socioeconomically characteristics of the patient, past medical history, current treatments, allergy information, prescription refill information, insurance information, and the like. Patient medical history may include, but is not limited to: previous prescriptions, known allergies, past medical history, insurance information, medicine regimen schedules, and/or refill schedules. Patient data may further include physical and socioeconomically attributes of the patient. Physical attributes of the patient may include but is not limited to age, sex, height, and known physical disabilities. Socioeconomic attributes of the patient may include but is not limited to employer history, patient previous residence and geographic information, and/or payment history and insurance information. In some embodiments, patient data 116 may correspond to one or more users. For example, each medication module 140 may be utilized by two or more users each having their own medication care plan and medicine regimen, which is discussed in further detail below.

In some embodiments, system 100 may include medication management database 114 API services 118. In some embodiments, API services 118 may include drug database services 118A, e-prescription services 118B, physician/hospital services 118C, and pharmacy/pharmacists services 118D. System sever 118 may connect to additional APIs or other cloud services including other essential and value added services (not shown). For example, value added services may include but are not limited to associated products sales, advertising and shopping links, affiliate marketing such as: grocery/food delivery; transportation, errands, house, yard, and housekeeping arrangements, telehealth services, and the like. Other value-added services include doctor appointments and event reminders, remote monitoring, voice assistant (e.g., Alexa, Siri, etc.) and voice commerce.

In some embodiments, system server 110 include access to API services 118 stored on database 124. System server 110 may support medication management module 140 and provide integrated medication management services via API services 118, including but not limited to adherence and noncompliance monitoring, prescription refill services, and caretaker functionality, which are discussed in further detail below.

In some embodiments, exemplary system 100 may, for example, employ a preferred network of preferred healthcare professionals corresponding to hospitals/physician 120 and pharmacist/pharmacy 130. Information related to the preferred network of healthcare professionals may be stored as API services 118. For example a particular hospital vendor may have a corresponding application in hospital/physician API services 118B. By accessing hospital/position API services 118B, a patient, system, or any authorized user may directly contact the hospital for updating prescriptions and/or seeking further information directly from hospital 120.

In some embodiments, a user of exemplary system 100 may input their personal information, which may be stored as patient data 116. Patient data 116 may correspond to medical information of patients utilizing system 100. Inputting patient data 116 may be accomplished in various methods. For example, inputting patient data 116 via mobile device 149, via graphic user interface 114 of medication management module 140, input and transmitted by hospital 120, utilizing speech recognition commands and a speech processor (e.g., speech processor 210 of FIG. 2 discussed below) in addition to GUI 114, and/or input in any other method that allows for transmission of patient data 116 from an input source (e.g., home desktop computer) to system server 110

In some embodiments, patient data may also be stored in memory 143 of medication management module 140, and/or mobile device 149. Patient data 116 may include physical characteristics of the patient such as age, weight, race/ethnicity, blood type, hair/eye color, and/or height, and also may include previous medical and surgery history of the patient. In some embodiments, components of system 100, including medicine management module 140, may communicate patient data 116, patient medication plans, and/or pill dispensing schedules based on the medication plan to any other parts of system 100.

In one embodiment, system server 110 may receive patient data 116 information from hospital 120, and pharmacy 130, and medication management module 140. System 100 may store patient data 116 including medication plan information on local device storage (e.g., mobile device 149 and/or module 140) in addition to the database 124 stored on system server 110. Doing so may be beneficial in the case where internet connectivity may not be available at the time of pill dispensing.

In some embodiments, system server 110 may provide API services 118. API services 118 may include services related to medication management and patient care. For example, in some embodiments, system server 110 may provide a prescription services 118 A, physician/hospital services 118 B, pharmacy/pharmacist services 118 C, and/or other services 118D. In one embodiment, electronic prescription services 118A may correspond to functionality for filling, adding, modifying, renewing prescriptions corresponding to patients utilizing system 100 issued electronically by physicians, or other authorized staff at hospital 120. Electronic prescription services 118 may include functionality that receives, maintains, and provides health care, for example e-prescription services 118 may notify users and other components of system 100 have potential drug interactions, dosage level modifications, and patient-specific factors including adverse drug reactions and allergies. Pharmacy/pharmacist services 118 C may include providing real-time video link to a pharmacists via graphic user interface 147, or other access methods, for example.

As discussed in further detail below, exemplary system 100 receive medication and treatment information from hospital 120 and pharmacy 130 and actively provide medication management services (e.g., API services 118). For example, in response to receiving updated prescriptions from hospital 120 and/or pharmacy 130, system server 110 may implement various medication management functionality. In one embodiment, medication management functionality may include preventing adverse drug interactions/reactions, promoting medication plan adherence, and monitoring and/or reporting for noncompliance, which is discussed in further detail below.

For example, upon receiving new and/or updated prescription information, server processors 112 may further determine the potential for any dangerous drug interactions and alert the user of any potential drug interactions (e.g., utilizing mobile device 149, and/or module 140, to issue an alert to the user). In some embodiments, server processors 112 may refer to drug database services 118C in order to determine potential drug interactions including drug to drug interactions and also interactions with to over-the-counter drugs and/or vitamin and dietary supplements that may cause adverse drug reactions with a patient's prescriptions. Server processors 112 may perform drug interaction determinations upon receiving patient data and prescription information for example utilizing prescription services 118A.

In one embodiment, system server 110 may receive prescription corresponding to users/patients and transmit said prescription to pharmacy 130. Upon receiving a prescription request from system server 110, pharmacy 130 may prepare medication in the form of pill cartridges, which is discussed in further detail below. As discussed in further detail below, in some embodiments, pharmacy 130 may ship medications and pill cartridges for use medication management module 40. Medication management module 140 may receive pill cartridges and dispense pills in accordance with a predetermined medication management care plan.

As shown in FIG. 1, medication management module 140 may include one or more processors 142, memory 144 storing software code 145 thereon, and graphic user interface 147. Software code 145 may include non-transitory machine readable instructions that, when executed by processors 142, cause medication management module 142 to implement medication management functionality in accordance with one or more embodiments described herein. In some embodiments, medication management module 140 may communicate with mobile device 149 and indicators 146.

In some embodiments, mobile device 149 may include a smart phone, laptop, tablet, notebook, or any other mobile computing device capable of establishing an Internet connection for receiving, processing, and transmitting commands and data. As shown in FIG. 1, indicators 146 may include audio indicator 146A, visual indicators 146B, and/or wearable indicators 146C. In some embodiments, indicators 146 may be integrated with $3^{rd}$ party platforms (not shown), products, and/or services (e.g., Headphones, speakers, phones, appliances, virtual/voice assistants (e.g., Amazon's ALEXA™/ECHO™), smart light bulbs, alarm, clocks, home monitoring devices, and the like).

In some embodiments, indicators 146 may receive indication commands from medication management module 140. In response to receiving indication commands, indicators 146 may indicate to the patient that it is time to take the medicine and/or notify of any upcoming appointments, announcements, and events. In addition to indicators 146, mobile device 142 may also indicate to the patient that is time to take the medicine and/or other notifications and events. For example, utilizing audio, visual, tactile indication and/or vibration functionality of the mobile device 149, a patient may be alerted that it is time to take the medicine.

In some embodiments, medication management module 140, utilizing indicators 146, may indicate to the patient that it is time for perform their medication care plan and prepare for dispensing medication. Many patients may be elderly patients that are hard of hearing and/or hard of sight. Thus, in some embodiments, indicators 146 may be positioned throughout a patient's environment (e.g., house, room, or any other place the patient may be located). For example, audio indicator 144A may include one or more speakers (or other audible/personification apparatus), with or without visual indicators 144B and/or wearable indicators 144C, positioned throughout the patient's environment.

Medication management module 140 may transmit an indication command to audio indicator 144A, with or without visual indicators 144B and/or wearable indicators 144C when it is time for a patient to take the medicine based on a predetermined medication regimen. In response to receiving the audio indication command, audio indicator 144A may sound an audio alert throughout the patient environment. The audio alert may include a song, a chime, a verbal command, recorded message, or any other sound that the patient can hear and understand to mean that it is time to take their medication and/or remind of any upcoming appointments and events. For example, in one embodiment, the recorded message may include a voice message recorded by family members, caregivers, physicians, or any other person whose voice my capture a patient's attention and encourage action.

In one embodiment, exemplary system 100 may include one or more visual indicators 146B. Visual indicators 146B may be positioned throughout a patient's environment and configured to provide a visual indication to the patient that it is time to take the medicine. For example, some patients may be hard of hearing and may not be able to hear an audio alert. Accordingly one or more visual indicators 146B may be utilized for providing a visual indication to the patient and is time to take their medicine. Visual indicators 144B may include one or more LEDs or other types of light generating devices. In some embodiments medication management module 140 may transmit an indication command to visual indicator 144B in response to determining that it is time for the patient to take the medication regimen. In response to receiving the indication command, visual indicator 144B may provide a visual indication to a patient that is time to take the medicine. For example visual indicator 144B may include an LED configured to flash red light, or other color of light (e.g., blue, green, yellow), at a predetermined interval in order to signal to the patient that is time to take the medication.

In another embodiment, exemplary system 100 may include one or more wearable indicators 146C. Wearable indicators 146C may provide a physical indication to the patient that is time to take the medication. Wearable indicators 146C may, for example, include a tactile indication module that may provide a tactile indication that the patient can feel on their body. Wearable indicators 146 may include a vibration motor that may vibrate to alert the user of medication times. The wearable device may vibrate and produce a vibration to the patient that it is time to take their medication.

As discussed in further detail below, in one embodiment, indicators 146 may utilize proximity sensors contained within indicators 146 in order to determine the location and/or proximity of the user. In response to determining the proximity of the user indicators 146 may adjust the level, volume, and/or intensity of the alert issued to the patient. In some embodiments, proximity sensors may be contained within management module 140 may be utilized in order to determine the location and/or proximity of the user. Level, volume, and/or intensity of the alert may be adjusted in response to the proximity of the user detected by proxy sensors of management module 140.

Figure 2:
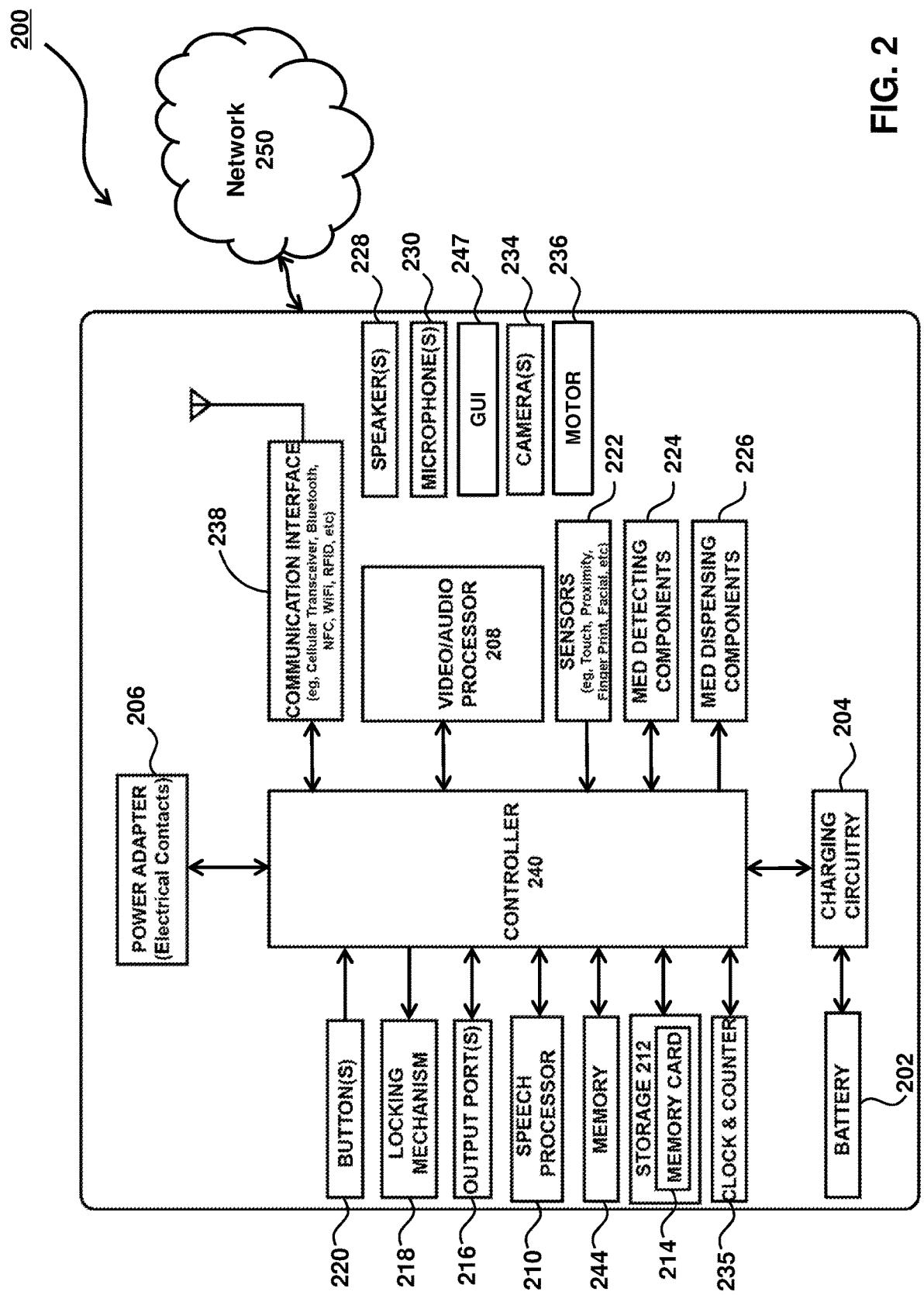
FIG. 2 is a schematic representation of exemplary circuitry for an integrated medication management module in accordance with one or more embodiments.

Referring now to FIG. 2, FIG. 2 depicts a schematic for an exemplary medication management module 200 in accordance with one or more embodiments described herein. Medication management module 200 may correspond to medication management module 140 of FIG. 1, of which similarly labeled parts and numbers correspond to similar features having similar functionality. As shown in FIG. 2, medication management module 200 may include battery 202 coupled to charging circuitry 204 and power adapters 206 configured to provide electrical power (e.g., AC and/or DC current) to management module 200.

In some embodiments, medication management module 200 may also equipped with output/input ports 216 for data transfer if needed and power adapter 206 to power source for medication management module 200 to be operable and/or charge its internal battery 202. Output/input ports 216 may also include a hardwired telephone jack, USB ports, serial ports, parallel ports, audio ports, video ports, VGA port, a digital video interface (DVI) ports mini-DVI ports, display ports, FireWire ports, Ethernet ports, RJ-11 motor ports and the like.

Medication management module 200 may further include controller 240, video/audio processor 208, speech processor 210, storage 212 having memory card 214 thereon, output ports 216, locking mechanism 218, buttons 220, sensors 222, medication detecting components 224, medication dispensing components 226, audio speakers 228, audio microphones 230, graphic user interface 247, cameras 234, 3-axis accelerometer/gyroscope 235, communication interface 239, and vibration motor 236.

In some embodiments sensors 222 may include proximity sensors, optic sensors, biometric sensors that can recognize fingerprint, facial, and/or other biometric signatures of the user. Medication detecting components 224 may include optic sensors and cameras and/or may work in conjunction with cameras 234 and sensors 222. In some embodiments, cameras 234 and/or medication detecting components 224 may include solid-state cameras utilize for machine-vision applications. Cameras 222 may include frame-transfer and/or interline-transfer charge-couple devices (CCDs), CMOS active-pixel sensors. Cameras 222 may include time-delay-integration (TDI) based cameras for machine vision, fast-framing devices for high-speed inspection, and back-a limited high-resolution cameras. In some embodiments, cameras 222 may include linescan cameras and/or area-array cameras. Optic sensors of sensors 222 may include photodetectors, fiber optics, proximity detectors, infrared, and or other types of light sensing devices.

In some embodiments, communication interface 239 may include but not limited to a cellular transceiver, Bluetooth, NFC, Wi-Fi, and/or RFID. In some embodiments, medication management module 200 may include Bluetooth tethering and/or telephone dial-up functionality utilizing communication interface 239 and output ports 216, respectively. For example, some elderly patients do not subscribe to cable Internet, module 200 may not have access to broadband Wi-Fi. Accordingly, users may plug module 200 into a telephone jack for data using output ports 216. In one embodiment, utilizing Bluetooth functionality of communication interface 239 caregivers may use their smartphone's Bluetooth (e.g. to tether module 200 for updating patient data and performing functionality related to medication and care (e.g., API services 118).

Medication management module 200 is configured for providing integrated care management in accordance with one or more embodiments described herein. For example, when scheduled dosage is due, medication management module 200 will alert the patient (care recipient) and/or caregiver (also referred to user herein) using a generic or customizable audio alert, song, or any audible tones together with visual alerts. For example, audible and visual notifications may be output from built-in speakers 228, and GUI 247 could be used to notify users of scheduled medicine time. Notifications (e.g., audio, visual, and/or vibration) could also be on user's smart devices' speakers and display screen (e.g., mobile device 149). In some embodiments, GUI 247 may include a touch and/or non-touch LCD, OLED, or flexible e-paper, alone and/or in combination (e.g., part OLED and part e-paper). In some embodiments, buttons 220 may include a one-touch dispense button 220. 1-touch dispense button 220 may release a grouping of medications at a predetermined time based on a patient's medication regimen. In one embodiment, dispensing medications may require authenticating utilizing biometric authentication, for example facial recognition, voice recognition, fingerprint recognition, and/or other biometric methods of verifying identity.

Sensors 222 may include proximity sensors 222A. Proximity sensors 222A may also detect whether anyone in the near vicinity of medication management module 200. Based on the user's proximity to medication management module 200 Volume of audible notification and/or intensity of visual alert (including selection of certain colors of light e.g. red, blue, green) may be automatically adjusted based on detection of human proximity and/or user settings. For example, in response to determining that it is time to take medicine, medication measure model 200 may utilize proximity sensors to determine the proximity of the user. In response to determining a near proximity (i.e., closer than a predetermined threshold distance) of the user, medication management module 200 may issue alerts on a minimum setting. For example low-volume audio, and low intensity of visual and tactile alerts. In response to determining that the user is a far vicinity (i.e., farther than a predetermined threshold distance), medication management module 200 may issue alerts on a maximum setting. For example high-volume audio, and low intensity of visual and tactile alerts.

In some embodiments, when a user travels from one geographic time zone to another, module 200, utilizing connectivity features and clock 235, may automatically adjust its internal clock 238 and dispensing schedule upon receiving data connectivity information corresponding to a new geographic time zone. In one embodiment, a user may manually adjust module clock 238 in order to account for time zone changes when moving through different geographic time zones.

In some embodiments, medication management module 200 may be configured for providing adherence and non-compliance monitoring. For example, when a patient or caregiver arrives to medication management module 200, a patient or caregiver may be required to push button 220 to unlock the locking mechanism 218. Doing so may activate the medicine dispensing component 116 to dispense the appropriate dosage. In some embodiments, medication management model 200 may determine when it is time to take medications according to the medication care plan, utilizing a clock and counter 235. For example, when it's time for patient/user to take medicines that is recorded with its internal clock and counter 235. In some embodiments, clock and counter 235 may be omitted and the system could leverage the internal storage 212 to keep track of a patient's medicine schedule and dosage. In some embodiments, patient/user info and medication care plan may be stored on storage 212. In this manner, medication management module 200 may be operable even when internet connection is lost or not present.

In some embodiments, the medicine detecting components 224 may record and analyze the types of medication and number of pills/dosages in the medication care plan is correct for patient's safety, for example, by identifying dangerous drug interactions and alerting the user, pharmacist, and/or Doctor. For example, via user setting input via GUI 247, patient or caregiver may configure the connected medication management module 200 to allow authorized users to dispense scheduled dosage via biometrics such as finger print, voice and/or facial recognition through built-in sensors 222 and speech processor 210, in addition to manual pass code entry.

In some embodiments, medication management model 200 may enable users to take pills "as-needed" (e.g., water pills, painkillers, vitamins, and the like). Utilizing GUI 147 and or voice command functionality via speech processor 210, medication management module 200 may dispense as needed pills whenever the user desires. In one embodiment, a user may configure medication management module 200 user settings to utilizing voice assistant to ask the user daily whether or not they would like to take as needed pills. In some embodiments, in response to a user inputting a voice or touch command, module 200 may dispense as needed pills at any time.

In some embodiments, various level of security may be configured by users (e.g., patients and caregivers). For instance, authorized patient or care recipient (e.g., elderly patients) may be authorized to dispense the medication within fifteen minutes (adjusted in user settings) of scheduled dosage time. In some embodiments, caregivers could have the ability unlock medication management module 200 to add/or remove medicines or make changes to dosage schedules at any time. This may be performed on medication management module 200 or on user's smart devices or computers (e.g., mobile device 149). Doing so may prevent medication abuse, ensure medication plan adherence, prevent patients from consuming incorrect dosages, and/or prevent non-authorized users from taking the medicines.

Figure 3B:
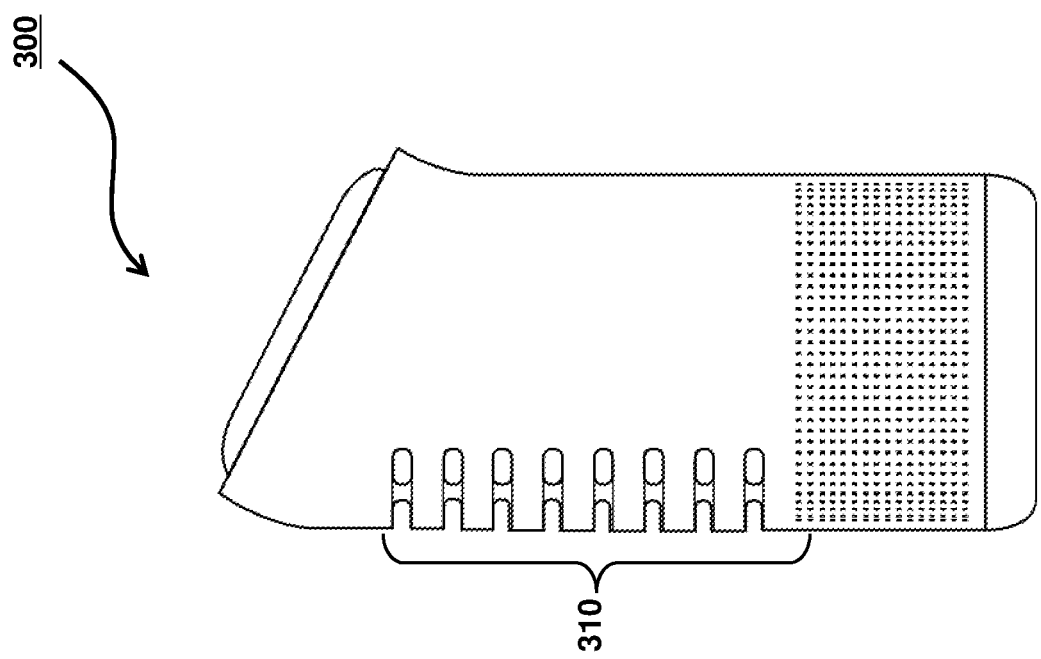
FIGS. 3A-3B are schematic representations of an integrated medication management module in accordance with one or more embodiments.
Figure 3A:
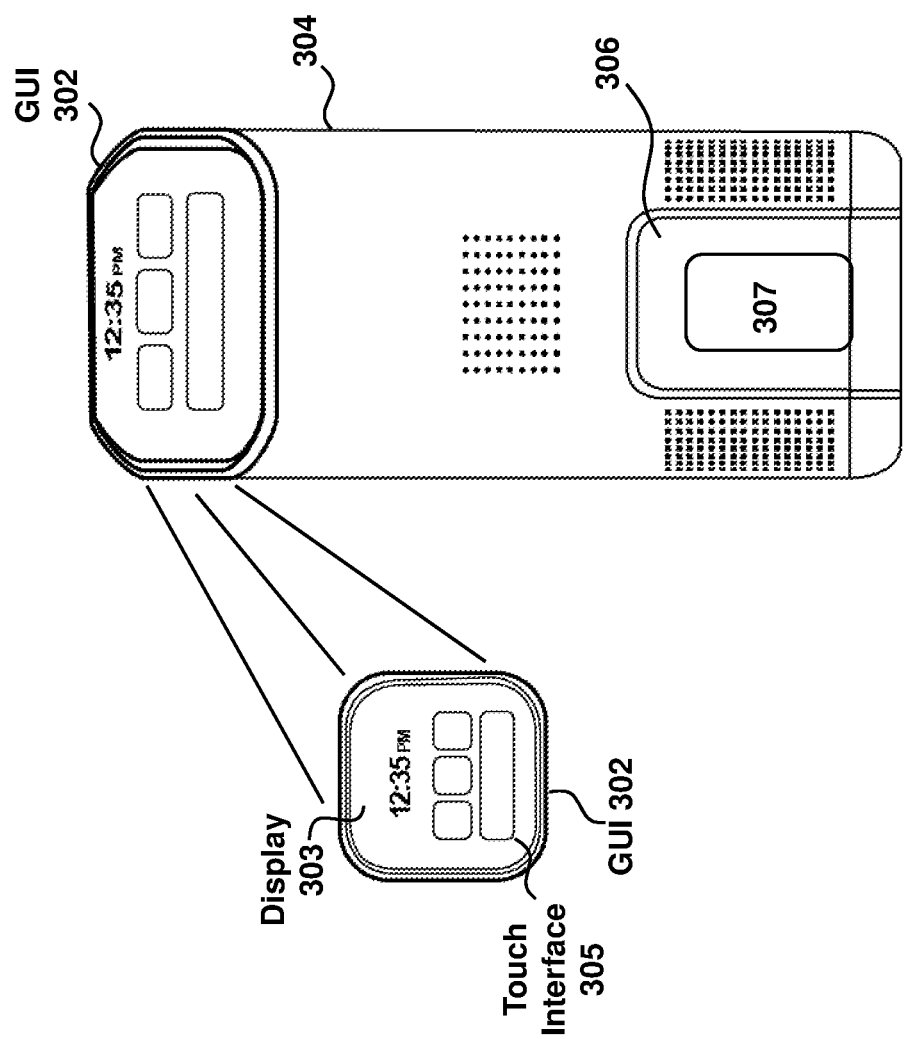

Referring now to FIGS. 3A-3B, FIGS. 3A-3B show a front view and a side view, respectively, of medication management module 300 in accordance with one or more embodiments described herein. As shown in FIGS. 3A and 3B, medication management module 300 may include graphic user interface 302 having display 303 and touch interface 305, housing 304, and dispensing area 306 and cup 307, and pill cartridge slots 310. Module 300 is depicted here having 8 cartridge slots, however in some embodiments module 300 may include more or less than 8 cartridge slots. For example, in some embodiments, module 300 may include 10 slots, or may include 5 slots.

In some embodiments, module 300 may be configured for modular use with one or more additional modules 300 (not shown). For example utilizing connectivity features (e.g., communication interface 239 and/or output ports 216) two or more module 300 may be combined and utilized in unison to provide as many cartridge slots as desired.

Figure 4A:
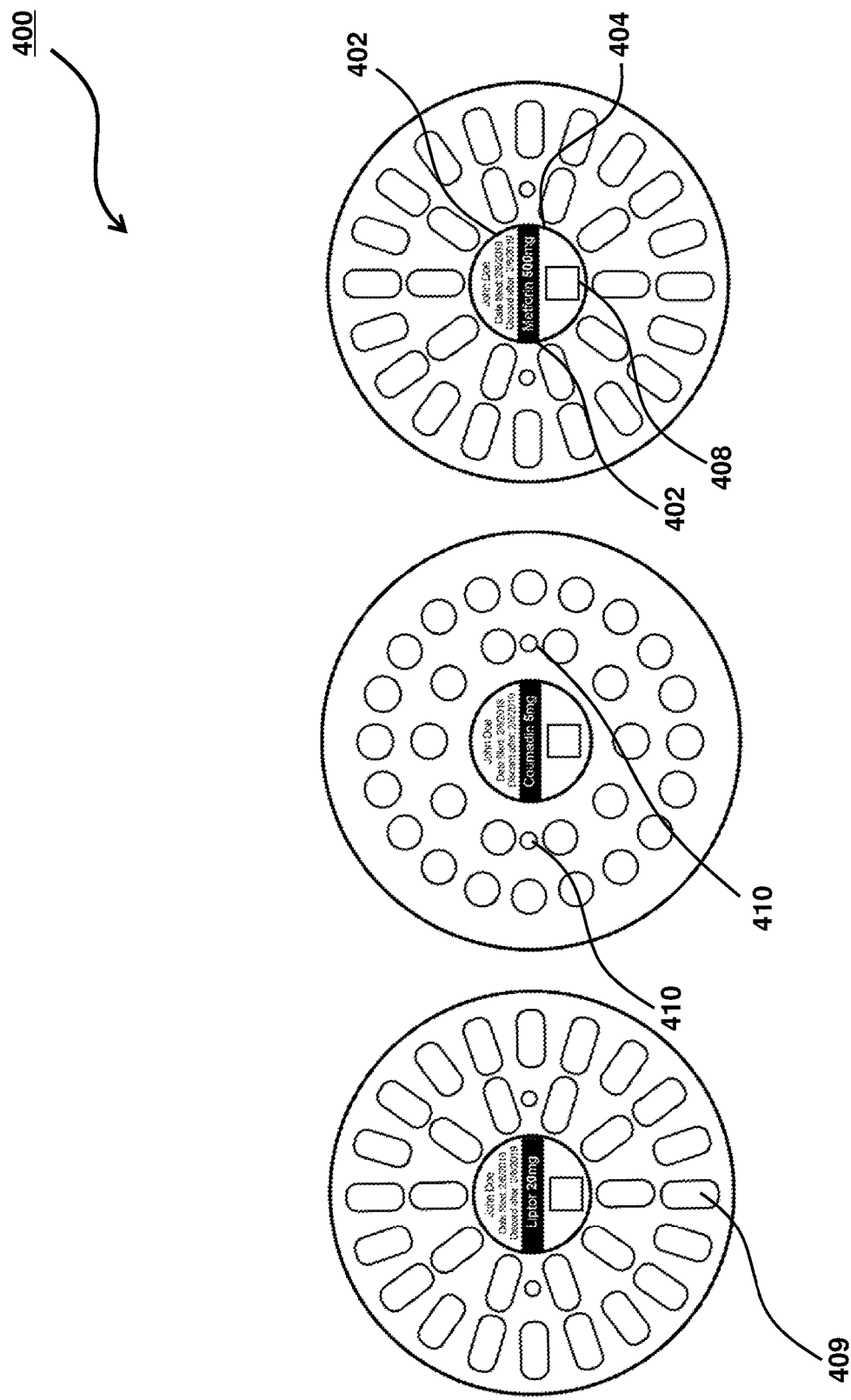
FIGS. 4A-4B are a schematic representation of an exemplary pill cartridge for use with an integrated medication management module in accordance with one or more embodiments.
Figure 4B:
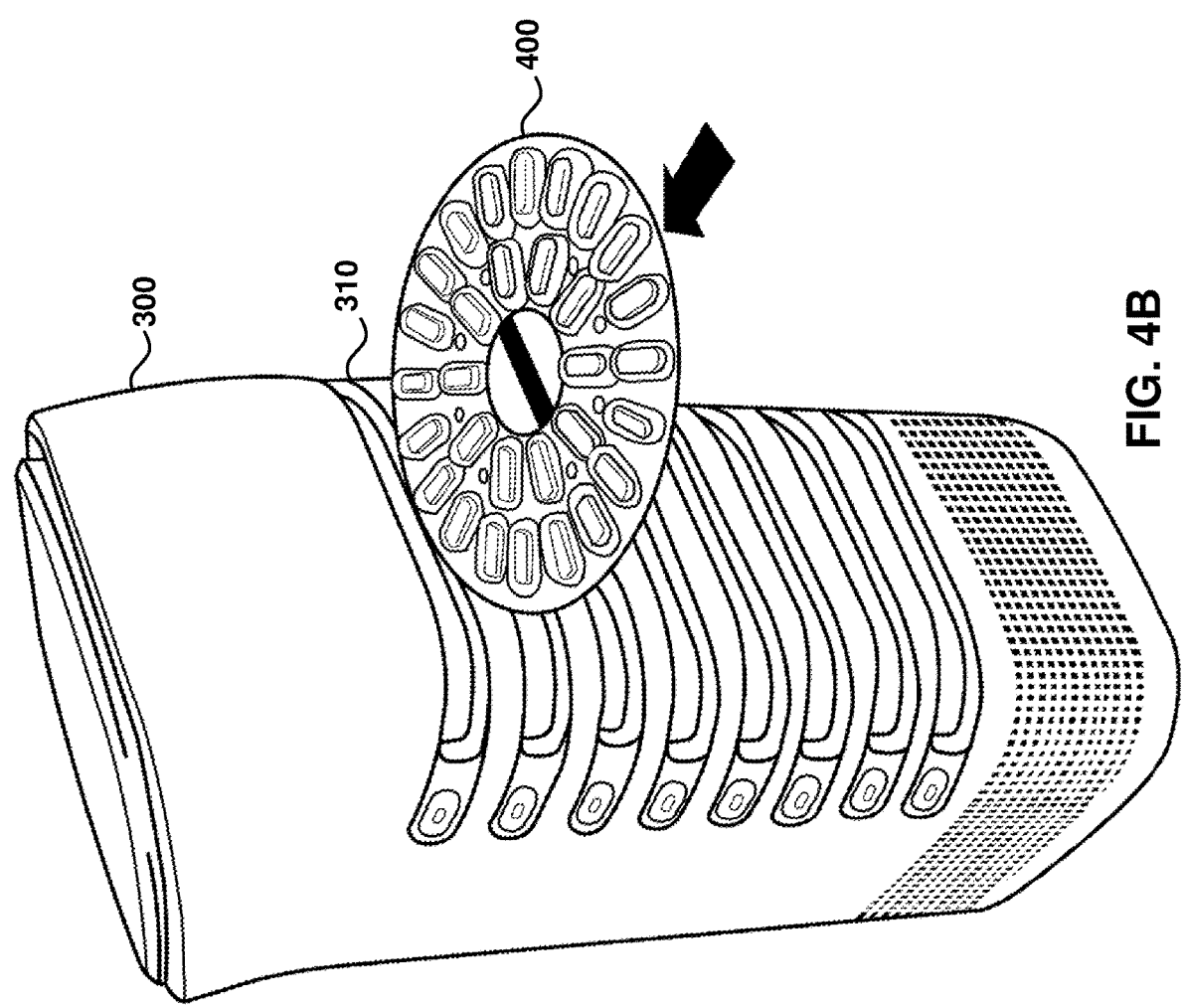

Referring now to FIGS. 4A-4B in conjunction with FIGS. 1-3, FIG. 4 depicts an exemplary pill cartridge 400 configured for use with a medication management module 140, 200, 300. Pill cartridges 400 may include patient ID 402, drug ID 404, drug dosage 406, label 408, and/or spindle apertures 410. Label 408 may include a QR label, RFID label, NFC, barcode, or any other identifying label/tag able to be scanned/detected and analyzed by inspection utilizing medication detecting components 224, sensors 222, and/or cameras 234. Label 408 may include provide information corresponding patient data 116, prescription information corresponding to the particular prescription for the user. Label 408 may also include IDs 402, 404, and dosage 406.

As shown in FIG. 4B, pill cartridges 400 are configured to be inserted into one or more pill cartridge slots 310 and loaded into module 300 for use in accordance with the medication care plan, which is discussed in further detail below. In some embodiments, medications on pill cartridge 400 may include 15, 30, 60, or 90 days of medication supply. Medication on a particular cartridge 400 may include one or multiple prescriptions corresponding to a particular user. In one embodiment, each blistered convex (i.e. pocket) may include one or more pills.

In some embodiments pill cartridges 400 may be package and filled by pharmacy 130 (either manually or via automation) as shown in FIG. 4A, patients and prescription information may be included and printed on a affixed label adhered onto or printed directly on cartridge 400. The exemplary embodiments described herein provide cartridges 400 that are designed for error proof insertion (for example a cornered box cartridge pill cards may be cornered and/or punctured and slots may be shaped in a way such that only pills facing up on cartridge 400 may be inserted into the device (e.g. slot 310). In some embodiments, using optic sensors and processors for storage, processors may remember the last position of a de-blistered pill pocket on a particular pill cartridge 400—even upon removal and reinsertion into a same slot 310 or different slot 310. Pill cartridge 400 may be inserted into any available slot 310, the slots 310 are not assigned to any particular prescription.

In some embodiments, upon insertion of cartridge 400 into a slot 310, medication management module 300 may cross-reference each cartridge 400 with patient data and determine a medication regimen and/or dosage schedule. Information on each cartridge 400 may provide patient and prescription data for medication management module 300 to implement. Prescription data may include the confines of how to take the medicine. Medication management module 300 may only dispense medicine within the confines of prescription data. For example, if the prescription requires no more than 2 daily, medication module 200, 300 will not dispense more than 2 of these types of pills daily. If cartridge 400 does not match patient data or if cartridge 400 is expired or outdated, medication management module 300 may automatically eject cartridge 400 and alert the user to remove cartridge 400. Upon receiving all cartridges, medication management module 300 may determine a patient care plan utilizing patient desired settings, patient data 116, and prescription data and drug information. The schedule may include the timing frequency and types of different medication.

In some embodiments, authenticating the one or more cartridges based on the patient data and the one or more pills comprises determining real-time adjustments to the medication regimen. For example, in some embodiments, utilizing a prescription services 118A, hospital 120 may update a patient's prescription in terms of dosage and/or removing or adding medication in real-time. In the event a patient's prescription has been updated, medication management module 200, 300 may be configured to automatically alert the user of an update, and/or discard any irrelevant medicine, and/or adjust dosages based on updated prescription information. For example, if a dosage was from 5 mg to 10 mg, medication management module may dispense two pills instead of one pill based on the updated medication prescription. This may happen in real-time using connectivity features of medication management module 140, 200, 300. In one embodiment, to dispense two pills of the same medication, module 200, 300 may accept two or more of the same prescription (pill cartridge 400) inserted in two or more slots 310 and may de-blister and dispense one pill from one cartridge 400 and de-blister & dispense another identical pill from another cartridge 400.

Discussed in further detail below, in one embodiment, upon automatically ejecting cartridge 400, cartridge 400 may be visually marked to show the cartridges invalid/outdated. For example, pill cartridge 400 may be automatically marked by dimple, aperture, perforate, ink mark, and/or other method by module 400 for user to easily identify that a cartridge 400 is invalid or empty and ready to be discarded. In this way uses will not mix up good and bad pill cartridges 400. In one embodiment, the user may be instructed to manually mark cartridge 400 upon being ejected.

Figure 5A:
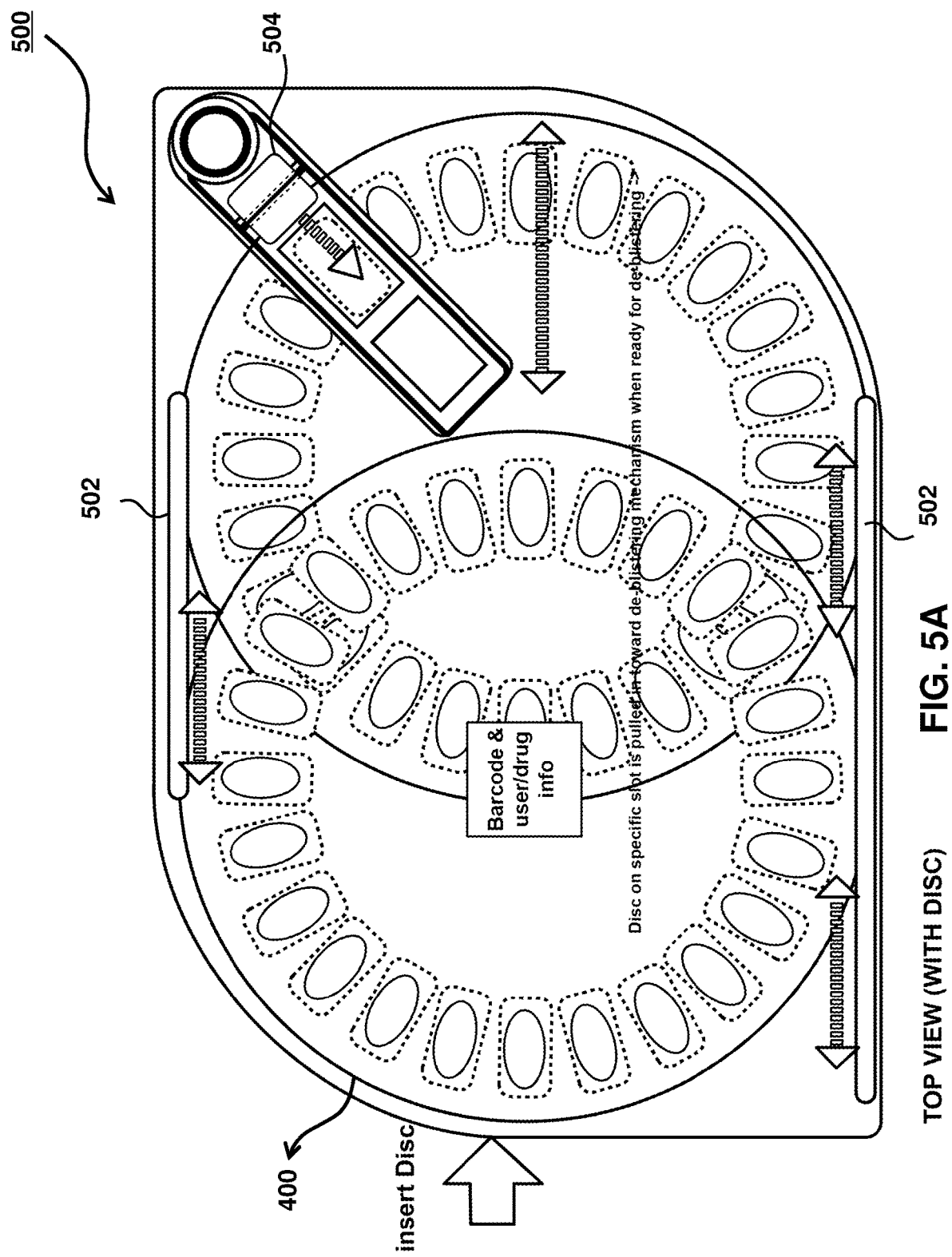
FIG. 5A-5B is a schematic representation of a pill extractor in accordance with one or more embodiments.
Figure 5B:
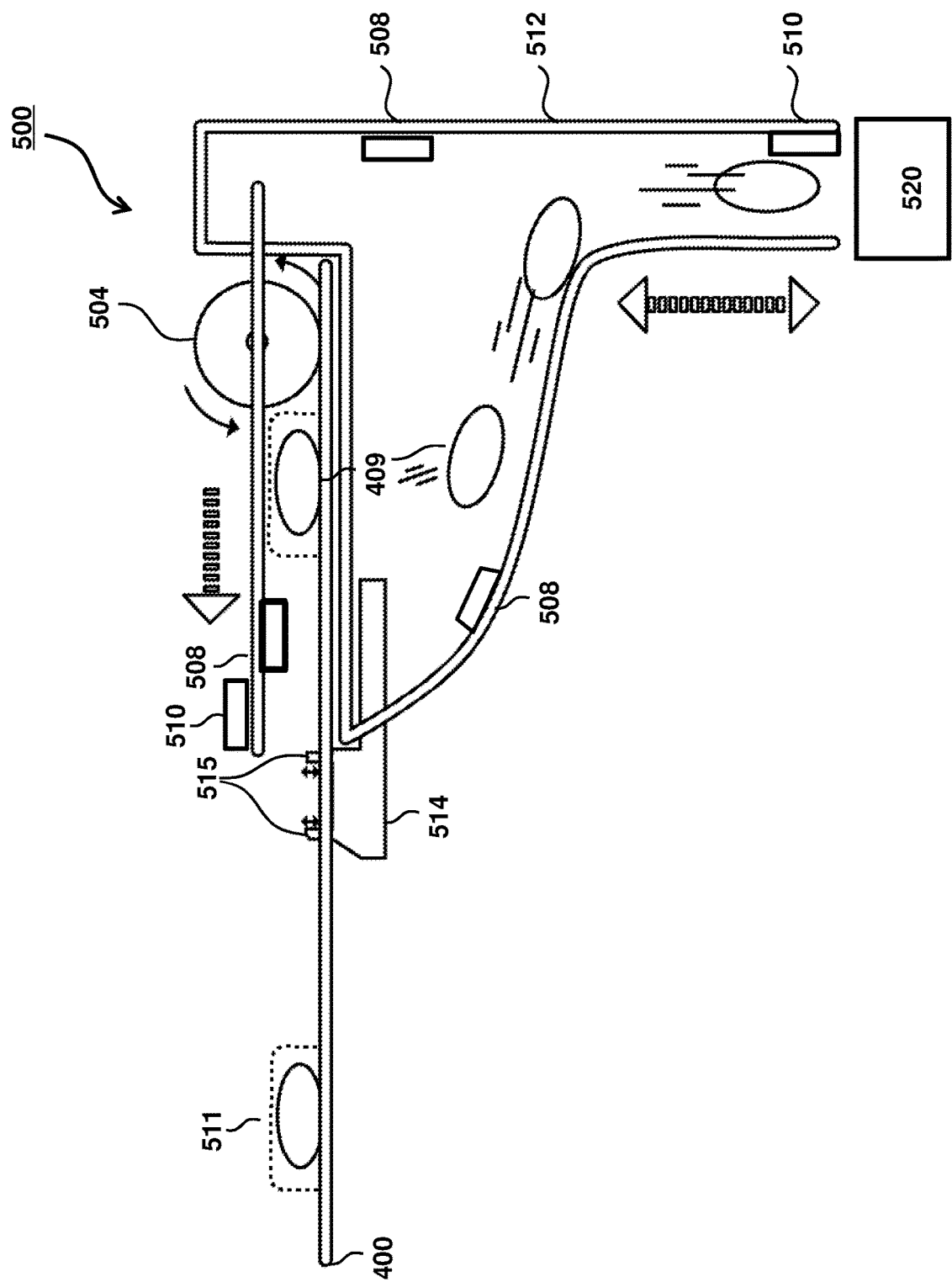

Referring now to FIGS. 5A-5B in conjunction with FIGS. 1-3, FIGS. 5A-5B depicts an exemplary extractor mechanism 500. FIG. 5A depicts a top view of the extractor mechanism 500, while FIG. 5B depicts a side view of extractor 500 depicting an exemplary pill cartridge 400 moving in and out of extractor mechanism 500 (depicted by the dotted line arrows). In some embodiments, extractor 500 may include two or more edged trays 502, marking mechanism 503, pill extractor 504, vibration motor 506, optic sensor/camera 508, optic sensor/camera 510, chute 512 spindle 514, pill holding area 520, and/or dispensing area 306.

As shown in FIG. 5A, extractor mechanism 500 may be configured for use with a pill cartridge 400. Pill cartridge 400 may be automatically pulled in upon insertion (e.g., similar to loading a DVD/CD). In one embodiment, cartridge 400 may be fastened and supported by edged trays 502. Spindle 514 may include one or more fingers 515. Spindle 514 may rotate until fingers 515 engage with punctures of cartridge 400. In one embodiment spindle 514 and fingers 515 may automatically spread outward to fasten cartridge 400 to be rotated. Pill extractor 504 may leverage its weight and push pill down to break the surface foil of cartridge 400. In one embodiment, extractor 500 may move up and down to a predetermined height where cartridge slots 310 may be individually utilized by extractor 500. In this manner only one pill extractor 504 is required for multiple cartridge slots 310. Discussed in further detail below, extractor 500 may be equipped with one or more optic sensors 508, 510 and a vibrational motor 506. Optic sensors 508, 510 and motor 506 may ensure proper pill dispensing and's report and monitor for adherence and noncompliance, which is discussed in further detail below.

In one embodiment, a user may be required to push pill cartridge 400 all the way in (similar to conventional SD card readers) for insertion. Cartridge 400 may be automatically or manually ejected. In one embodiment, Pill cartridge 400 may only be inserted in a specific way. For example, pill cartridge 400 can be inserted only with pills facing a predetermined position (e.g., facing up or facing down up). Therefore, if a user attempts inserting pill cartridge 400 with pills facing in the wrong direction, pill cartridge 400 cannot be inserted due to the design (shape) of the slot entry (e.g., pill cartridges slot 310 of FIG. 3). Cartridge 400 may be pulled in toward pill extractor 504 when medication is required to be administered, for example based on medication care regimen.

Barcode, QR code, RFID, or other cartridge unique ID detection may be integrated on the center, along the edge, or anywhere on cartridge 400. If pill cartridge 400 does not match patient ID or if Pill cartridge 400 is outdated/invalid or completely empty, cartridge 400 may be automatically ejected, per user settings, and ask user to remove the depleted or invalid pill cartridge 400. In another example, per user's setting, user will be prompted to remove a Pill cartridge 400 and upon interfacing with and instructing the device, that specific pill cartridge 400(s) will be ejected for removal. As mentioned above, in one embodiment, marking mechanism 503 may be configured to mark cartridge 400 upon ejecting. In one embodiment, marking mechanism 503 may mark and ejected pill cartridge 400. The mark may include a dimple, aperture, perforate, ink mark, and/or other method for user to easily identify that a cartridge 400 is invalid/outdated or empty and ready to be discarded.

In some embodiments, when pill(s) on a specific pill cartridge 400 needs to be extracted/de-blistered, pill cartridge 400 on that specific slot is pulled further toward the pill extractor 504 for pill(s) to be extracted. Spindle integrated with one or more fingers rotates until it finds the aperture(s)—and instantly spring out to fasten pill cartridge 400 to be rotated. Pill cartridge 400 is rotated to the correct position for the specific pill(s) to be de-blistered. Then pill extractor 504 (e.g., roller, wedge, puncture, etc.) will activated to de-blister/extract that specific pill(s). Extractor mechanism 500 may move from one row to another row where pill cartridge 400 has one or more rows of pills. In one embodiment, spindle 514 and fingers 515 may be omitted where pill cartridge 400 may be gripped and spun using motors on one or more edges or the center or an open space of pill cartridge 400.

In some embodiments, medication management module 140, 200, 300 may verifying the correct extraction of the one or more pills to ensure error-proof pill ministration. For example, utilizing one or more optic sensors (222) and/or cameras (234) to verify the correct extraction of the one or more pills. Verifying extraction and dispensing may be implement it utilizing optic sensors and cameras 508 510, and vibrational motor 506. For example, an optic sensor/camera 508 may be placed directly on extractor mechanism 500 near the roller 504. In this manner optic sensor/camera 508 may be positioned to identify a pill inside the pocket before being dispensed. Optic sensor/camera 508 may ensure the pill is properly aligned in pocket 511 such that roller 504 completely the blisters pocket 511 and dislodges pill 509.

In one embodiment, upon dispensing, the camera may verify that the pill 509 has completely and properly been released from the pocket 511 of cartridge. In one embodiment, utilizing machine vision and computer vision functionality for example, camera 508 may identify the pill as it is being extracted from cartridge 400 and pocket 511. Once pill 509 has been identified, the module may verify that the pill matches with the medication care plan to ensure that the incorrect pill was not placed into the cartridge 400, for example at the pharmacy. This will ensure that the cartridge 400 actually has the medicine that supposed to be in cartridge 400 and not a different medicine that has been erroneously placed into cartridge 400. This will also ensure the pill 509 has been completely extracted from pocket 511.

In some embodiments, another optic sensor/camera 508 may be placed on chute 512 adjacent to and/or directly underneath pocket 511 in order to verify the pill 509 is properly falling through chute 512 and is not stuck in chute 512. In one embodiment, optic sensor/camera 508 may also make sure there are no objects obstructing the functionality of extractor mechanism 500. For example, extracting pills from cartridge 400 may cause foil to build and cause an obstruction. Optic sensor/camera 508 may identify an obstruction and/or jam inside extractor mechanism 500 and alert the user of a potential obstruction.

In some embodiments, if/when optic sensor/camera 508 identifies that pill 509 is lodged in chute 512, medication management module 140, 200, 300 may activate a vibrational motor 506. The vibrational motor 506 may cause a vibration of chute 512 or vibration to pill cartridge 400 may dislodge a stuck pill 509 and allow proper dispensing of the pill. In another embodiment, vibration motor 506 may be activated any time pill extractor mechanism 500 is extracting pills.

In one embodiment, another optic sensor/camera 510 may be placed near holding area 520 may be utilized to store pills that are being dispensed at any one particular time. For example, based on the patient's medicine regimen, the patient may need to have many pills at one time. Extractor mechanism 500 may individually extract each pill that is required from one or more pill cartridges and store the pills in a holding area after they've been extracted until all the pills have been extracted that are needed per dispensing time. To further ensure complete elimination of error optic sensor/camera 510 may be placed in or adjacent to holding area 520. Once all the pills have been dispensed, optic sensor/camera 510 may analyze all the pills and the holding area and compare those pills to the patient's medicine regimen and patient data. By ensuring the all the pills in the group of pills match the patient data and medicine regimen, this again eliminates any potential for a patient to have the wrong medicine, or the wrong dosage, at the wrong time. Thereby eliminating the risk of overdosing or taking the wrong medication. In some embodiments, extracted pills may drop directly out to pill cup, without having to temporarily stored in pill holding compartment.

In another embodiment, the grouping of pills per dispensing time may be held in holding area 520 until the user commands the module 140, 200, 300 to dispense. The dispensed command may be input by one touch button, or by voice commands. Once the patient utilizes the debate dispensed command, optic sensor/camera 510 may take a snapshot of the pills in the dispensing area 310 after they've been dispensed and store the snapshot in memory 244. In response to the user activating dispensing functionality (e.g. one touch button 222, and/or voice commands utilizing speech processor 210 the pills 509 in holding area 520 may be released and dispensed the dispensing area 306. In some embodiments, if the patient does not utilize dispense functionality to dispense medication at the proper medication time or within a predetermined amount of time after the medication time, medication management module 140, 20, 300 may report noncompliance and/or adherence to hospital 120, and/or other caretakers.

Figure 6B:
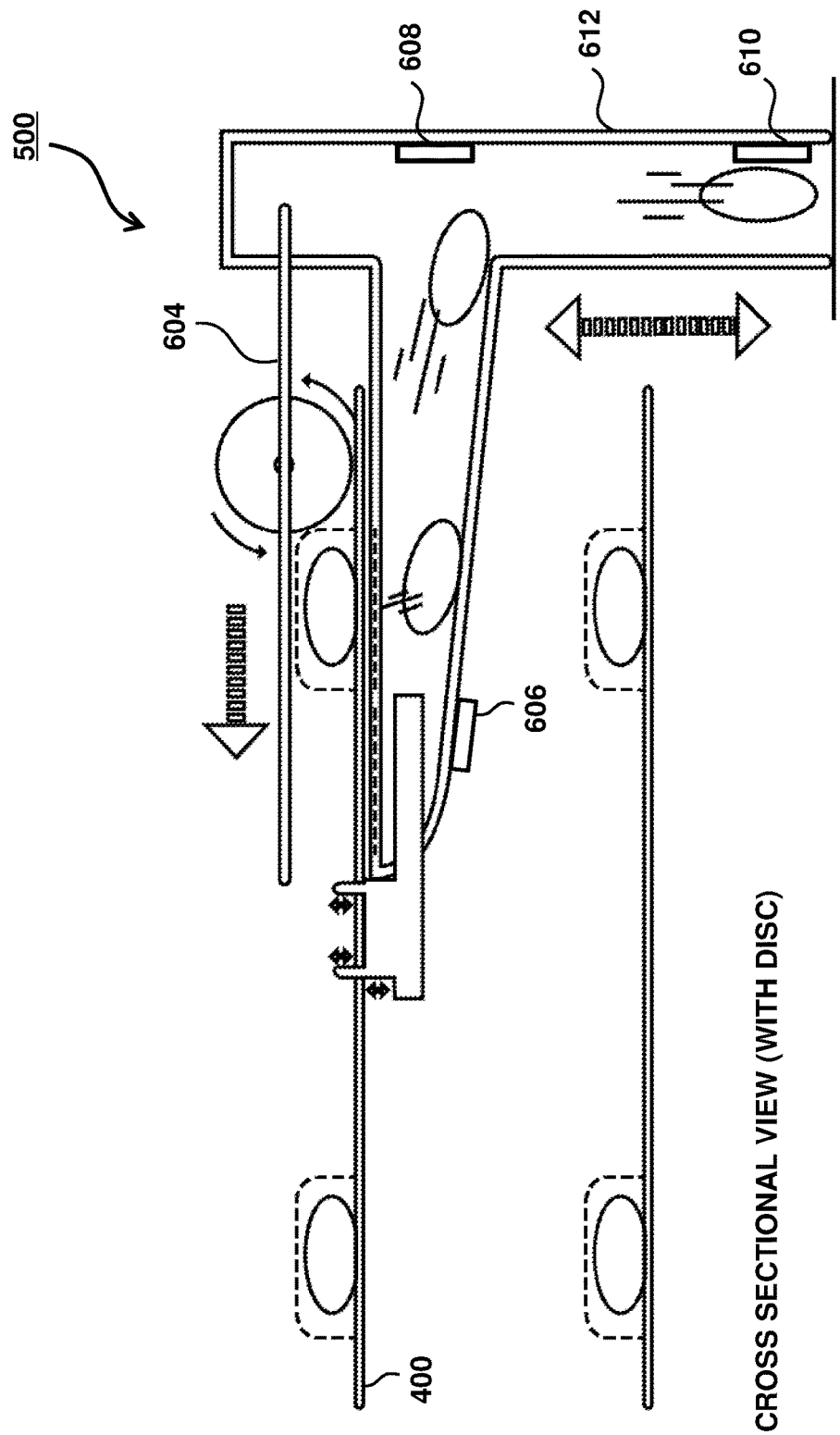

Referring now to FIGS. 6A-6B in conjunction with FIGS. 1-3, FIG. 6A-6B depicts an exemplary extractor 600 in accordance with one or more embodiments. Extractor 600 may operate like extractor 500 of FIG. 5, except that in this embodiment, cartridges 400 may be inserted automatically and engaged into individual slots 310. As shown in FIG. 6A, pill extractor 604 may pivot and rotate in order to not obstruct the movement of pill extractor 604 down through individual slots 310. As shown in FIG. 6B by the dotted vertical arrow, pill extractor 604 may cause de-blistering of a pill cartridge 400 and allow the pill to be dispensed down chute 612.

In some embodiments, extractor mechanism 600 may move to the corresponding slot (e.g., 310) for the pill(s) on particular pill cartridge 400 that needs to be extracted. Extractor mechanism 600 may turn to clearance area (so pill cartridge 400 do not block the movement of mechanism 600) to move up & down to another slot (or side to side, or any direction) where specific Pill cartridge 400 needs to be de-blistered. Pill extractor, 504, 604 may be fastened by one or multiple frames or bars or the alike. And it may be placed on the one side, both side, or center. Upon de-blistering/extracting, pills 509, 609 may be dropped to chute and temporary stored in an area waiting for user to dispense the dose. In another embodiment, de-blistered pill(s) 509, 609 may drop down and out to pill cup 307 simultaneously.

In some embodiments, vibrational motor 606 may ensure proper dispensing of pills by vibrating chute 612 and causing kinetic energy to pass to the pills and further ensure proper disposal down chute 612. In another embodiment, extractor 600 may include one or more optic sensor 608, 610. Optic sensor 608, 610 may inspect chokepoints of pill extraction and visually ensure proper pill dispensing, similar to the discussion above. Chokepoints may include any areas of chute 612 and/or other parts of dispensing mechanism 500, 600 that are likely or could potentially cause obstructions of pills falling through chute 612 into dispensing area 306. For example, in some embodiments optic sensor 608, 610 may detect obstructions and/or jams caused by foreign objects, for example from foil buildup due to the pill extraction process. In some embodiments, upon detecting an obstruction or foil jam, module 140, 200, 300 may be configured to issue an alert to the user that the module has an obstruction or jam.

Extractor 600 may include a single extracting pill extractor 604 that may automatically move to the corresponding slot(s) where pill(s) need to be extracted (e.g., from one slot 310 to another slot 310). In other embodiments, two or more extracting/de-blistering mechanisms could be used while different embodiments may employ one extractor mechanism per slot. Extractor 600 may include optic sensors/cameras to verify correct dispensing of pills, some of the discussion above.

One or more embodiments described herein provide for a medication management module 140, 200, 300 may remember the de-blistered pill convex (es)/pocket(s) on a particular pill cartridge 400 even if it removed and reinserted or partly de-blistered. In some embodiments, optical sensor(s) 608 and/or camera 610 may be used to detect and determine which pill pocket(s) had been de-blistered/extracted and which ones still the pill(s) enclosed. In some embodiments, camera 510 may also be integrated to capture an image of the dispensed pills (e.g., in a pill cup 307 located in dispensing area 306 of FIG. 3) and store and analysis the image in order to determine whether or not the correct medication has been dispensed. While FIGS. 5 and 6 depicts sensors and cameras as affixed to shoot 612, in some embodiments Optical sensor(s) 608/cameras 610 may be integrated with de-blistering 504, 604 and/or other parts of extractor 500, 600.

Figure 7A:
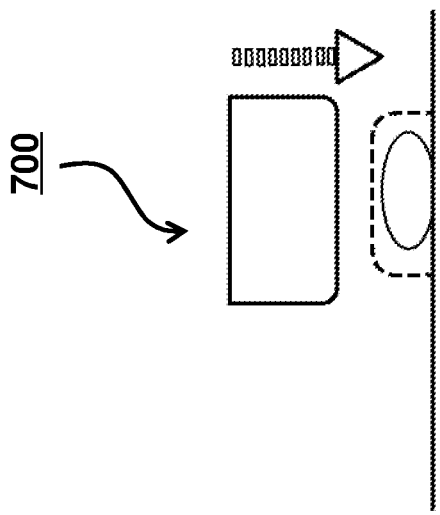
FIGS. 7A-7C are schematic representations of an extractor mechanism in accordance with one or more embodiments.
Figure 7B:
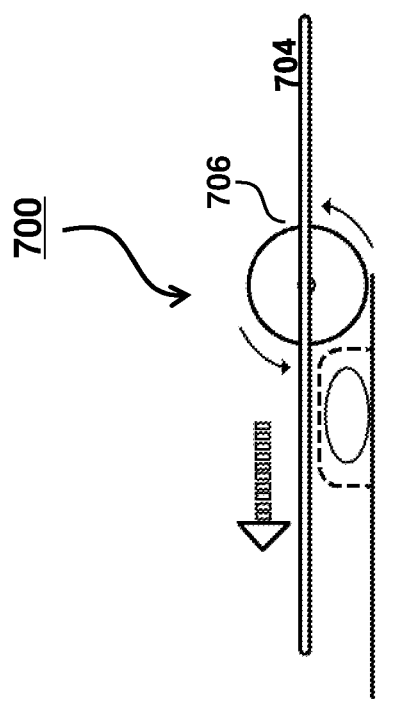
Figure 7C:
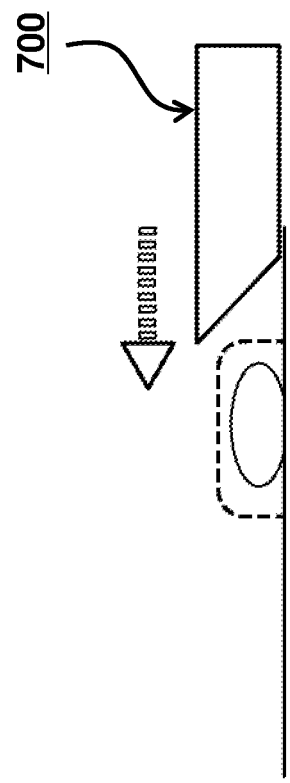

Referring now to FIGS. 7A-7C in conjunction with FIGS. 1-3, FIG. 7A depicts an extractor mechanism 704 having a roller 706 configured to roll over and extract pills from cartridges 400 (not shown in FIG. 7) utilizing the weight of the roller to force pill extraction. For example, cartridge 400 may be fastened in place (e.g., by edgy trays 502) while roller 706 moves out to force the pills to break foil and drop-down chute 512, 612. Roller 706 may be fastened with one or more frames or other methods of fastening the roller to extractor 504, 604.

In one embodiment, as shown by FIG. 7B, extractor mechanism may include a puncher that is configured to punch downward very quickly to force pills to break foil and drop-down chute 512, 612. The puncher may quickly return to a normal state. In some embodiments, cameras and/or optic sensors (not shown) may be integrated on the puncher to verify the correct extraction of pills.

Referring now to FIG. 7C, in one embodiment, extractor mechanism may include a wedge like extractor. The wedge-shaped the blistering component works similar to the puncher but the movement is horizontal from side to side rather than vertical from top to bottom. In some embodiments, cameras and/or optic sensors (not shown) may be integrated on the wedge like extractor to verify the correct extraction of pills.

In some embodiments, pill cartridges may include a container (e.g., 4"×4"×0.5"), housing a pill strip roll. Pill strip rolls may be configured for providing, for example, a 14, 30, or 90-day supply of blister packaged pills. Pill strips may be any length and width and could be formed by top and bottom foil layers foil together and may be used with or without a housing container. Container and pill strips may be any size, form factors and constructed in any materials. With pill information and/or barcode imprinted on container, pill cassettes may be constructed with a lower back corner angled for error-proof insertion can be removably inserted and removed from the cartridge slots. In some embodiments, pill information may be imprinted on pill strip, other packaging materials, or elsewhere.

While the above exemplary implementations are especially well suited for providing integrated medication care management, other variations and implementations of pill cartridge 400 and extractor mechanism 500, 600 can be implemented without diverting from the scope and spirit of the exemplary embodiments described herein, and have been fully contemplated. For example in some embodiments, pill cartridge and extractor mechanisms may include such as described in U.S. patent application No. 62/583,971 filed on Nov. 9, 2017, the contents of which are expressly incorporated herein by reference.

Figure 8:
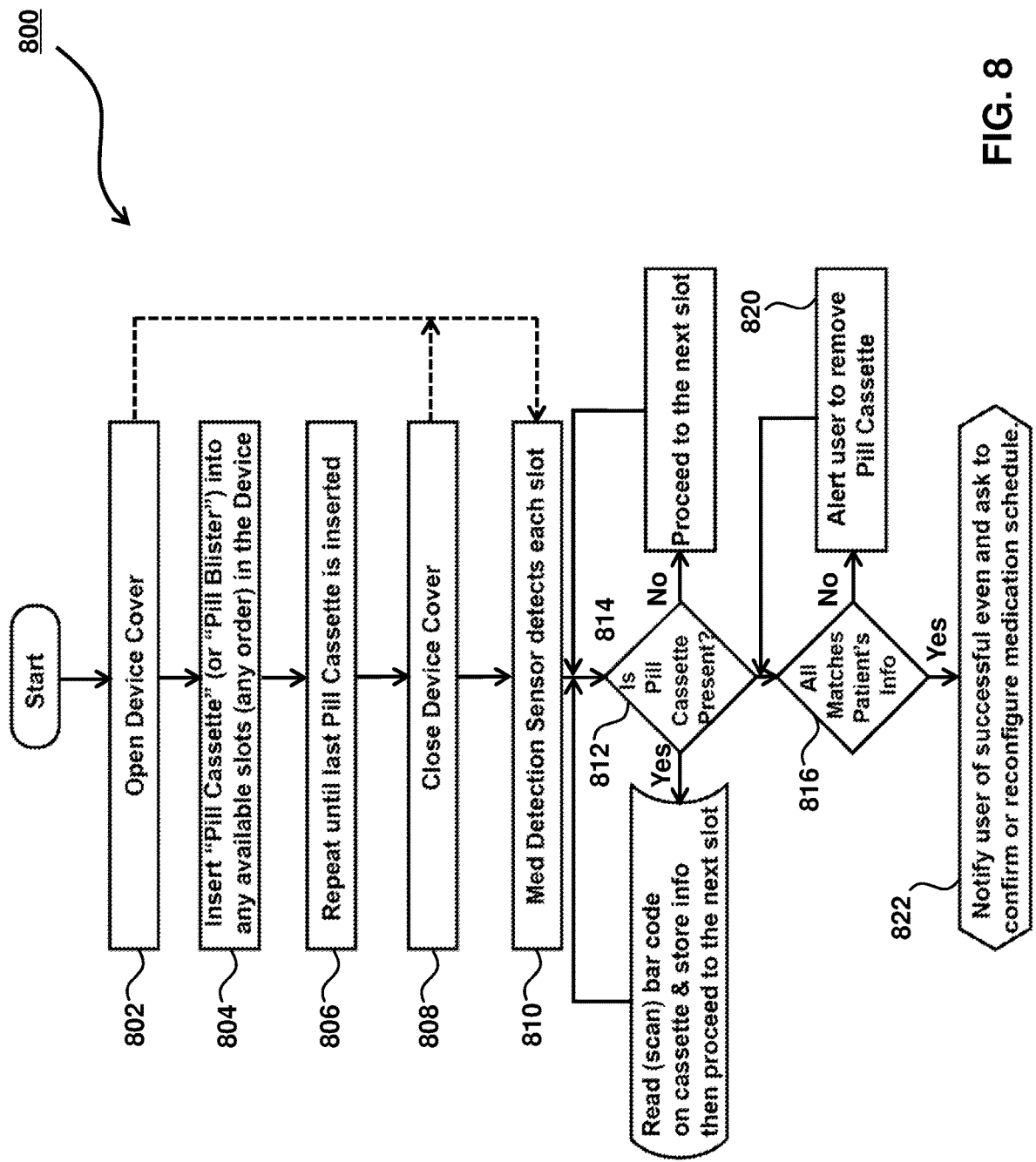
FIG. 8 depicts a method for integrated medication management in accordance with one or more embodiments.

Referring now to FIG. 8 in conjunction with FIGS. 1-4, FIG. 8 depicts exemplary method 800 for providing integrated medication and care management. Method 800 may begin at operation 802 wherein a user insert pill cartridge 400 into any available slot 310 in any order on module 300 and operation 806, repeat until last pill cartridge 400 is inserted. At an operation 810, medicine detection component 224 detects and determines a presence of cartridge 400 in each slot 310. When pill cartridge 400 is present in slot 310, at an operation 812, read (scan) barcode/label on cartridge 400 and store labeled information and proceed to the next slot 310. At an operation 814, when pill cartridge 400 is not present, proceed to the next slot 310. At an operation 816, determine patient data matching drug data. When there is not a match at an operation 820 alert user to remove pill cartridge 400. When there is a match, at an operation 822, notifying the user of successful event and ask to confirm or reconfigure medication schedule. Notifying and asking may be performed utilizing graphic user interface 147, 247, which is discussed in detail below.

Figure 9A:
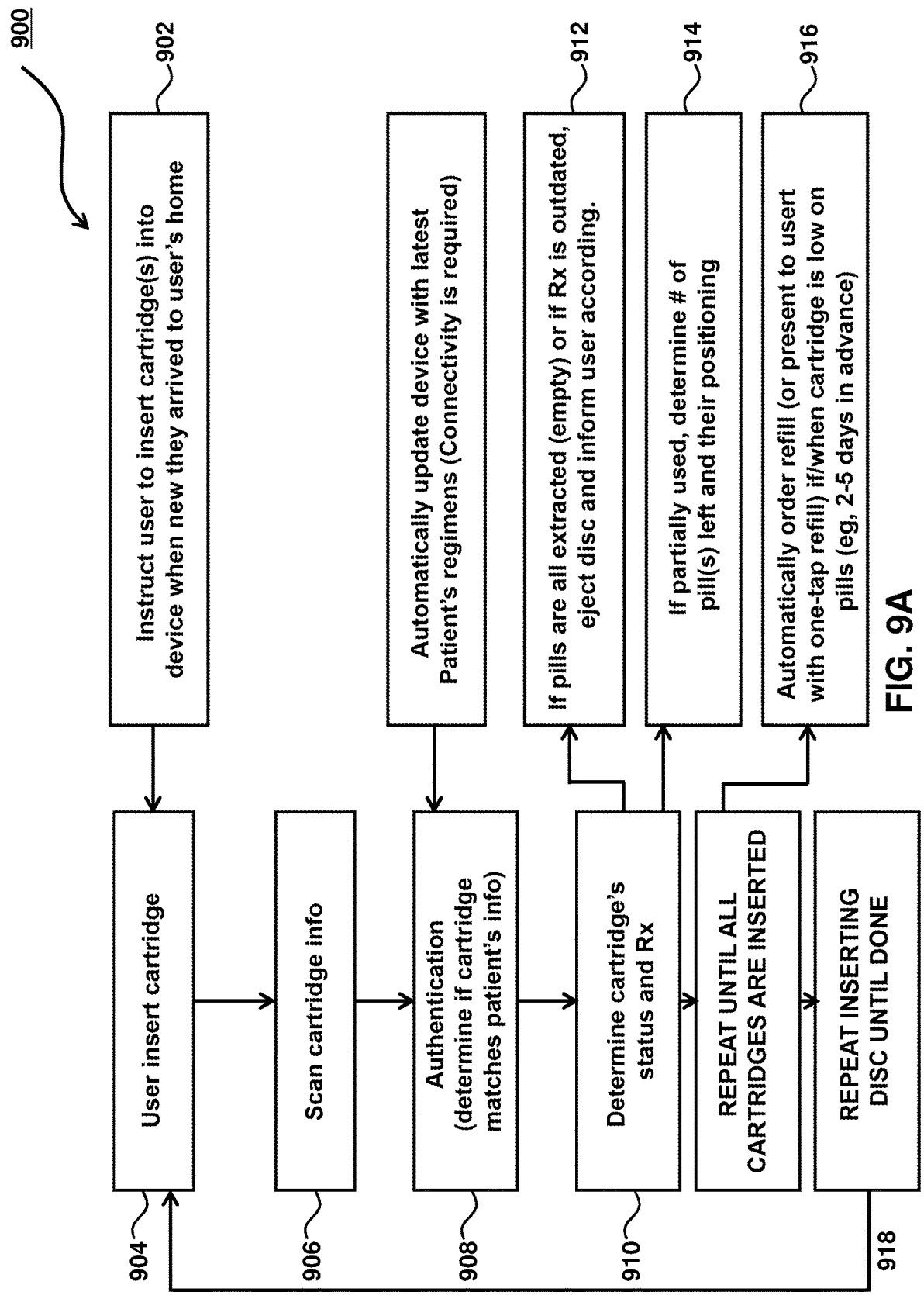
FIGS. 9A-9B depicts a method for operating at integrated medication management module in accordance with one or more embodiments.
Figure 9B:
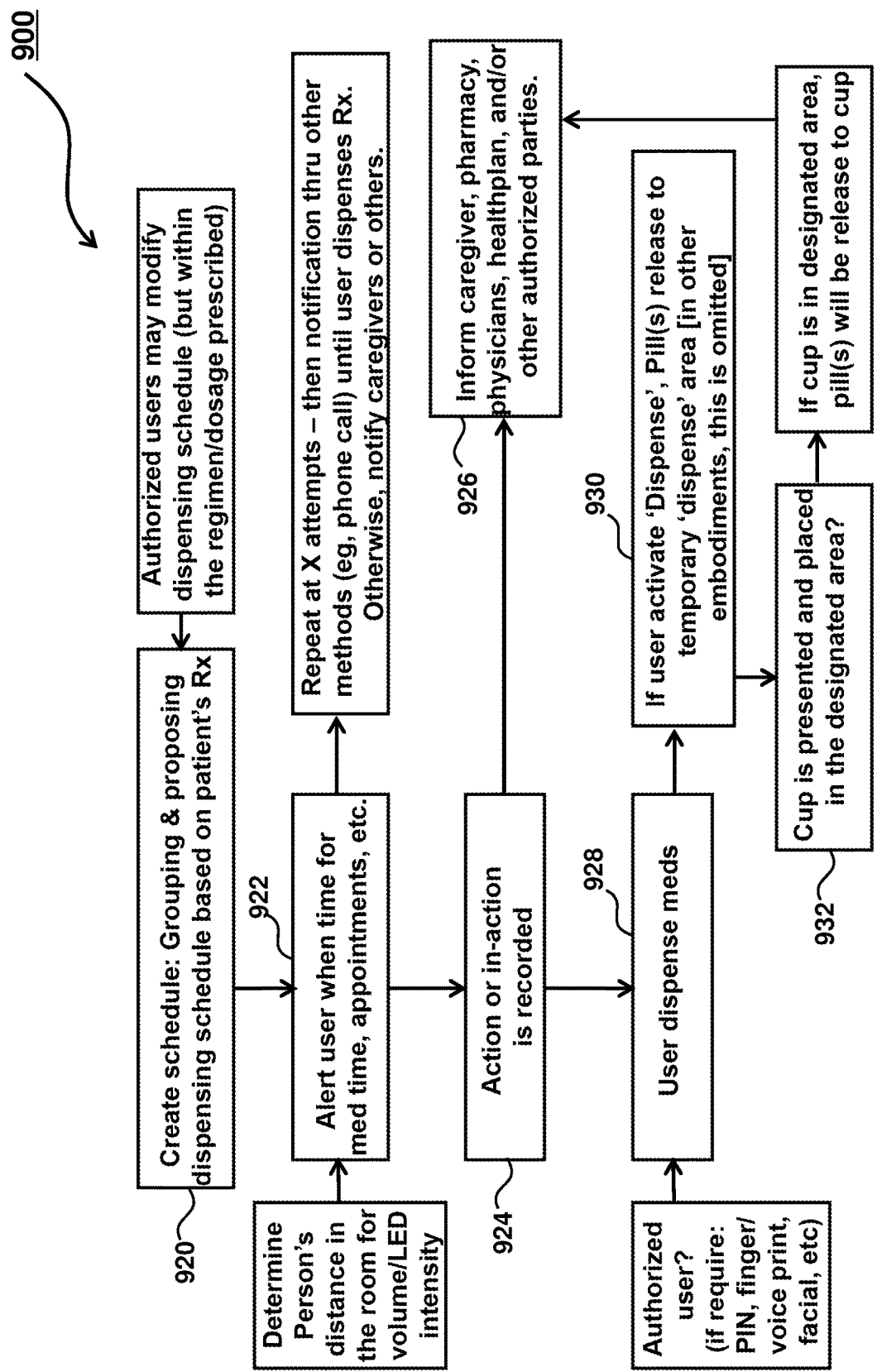

Referring now to FIG. 9 in conjunction with FIGS. 1-4, FIG. 9 depicts exemplary method 900 for providing integrated care and medication management. In some embodiments, utilizing connectivity features, medication management module 300 may be aware of the arrival of new medication (e.g., pill cartridge 400 received via mail/parcel/hand delivery, and the like) and may determine whether new cartridges 400 have been inserted. For example, in one embodiment pharmacy 130 may transmit an alert to module 140, 200, 300 that new cartridges 400 are on the way to the user's home. When a new cartridge 400 arrives at a user's home, medication management module 300 may alert and instruct the user to replace pill cartridges 400 in slot 310.

Accordingly, at an operation 902 module 300 may instruct a user to insert cartridge 400 into device 300 when new cartridges 400 arrive to the user's home. At an operation 904, user may insert cartridge 400 in slot 310. At an operation 906, module 300 may scan/read cartridge information 402, 404 on cartridge 400. At an operation 908, authenticate and determine if cartridge 400 matches patient data 116. In some embodiments this may include automatically updating module 300 with latest patient data and medication care plans utilizing connectivity features.

At an operation 910, determine cartridge status and drug data. If pills are extracted or empty, or if drugs (e.g., prescriptions, over-the-counter drugs, vitamins, dietary supplements, and the like) are outdated/expired, at an operation 912, eject disc and informed user accordingly. If partially used, an operation 914, determine and store number of pills remaining in the position of cartridge 400. If the cartridge 400 is empty or low (e.g., 2-5 days in advance), at operation 116 automatically order refill via e-prescription services 118A, or present to the user a 1-touch Refill button (e.g. utilizing graphic user interface and/or voice commands). At an operation 918, repeat until all cartridges are inserted.

At an operation 920 module 300 may determine and create a notification schedule by grouping various prescriptions and proposing a dispensing based on the patient's prescriptions, patient data 116, and patient user preferences. In some embodiments pharmacists and authorize users may modify dispenser schedules within the requirements of the prescription. In some embodiments, server 110 may authenticate an authorized user's request to modify a patient's regimen.

In some embodiments, a caretaker may request a change in the prescription/notification schedule from server 110. Server 110 may authenticate the caretaker request by verifying the caretaker (e.g., utilizing finger scan, voice notification, or other biometric identification). For example, server 110 may comprise a client-server computer system including a server computer connected to a plurality of medication management modules will 40, 200, 300 over a wide area network (network 150). In some embodiments, the server computer system may to store patient data corresponding to a plurality of patients having corresponding caretakers. Server computer system may receive an authentication request query comprising an authentication (fingerprint scan, voice notification, facial recognition, and/or other biometric verification), corresponding to a caretaker from at least one medication management module. The query may include a request to modify the medicine regimen and/or dosage/administration times. The client/server computer may determine an authentication status corresponding to the caretaker, and transmit, in response to determining the caretaker is authorized, a prescription modification command to the at least one medication management module. The prescription modification command may adjust the dosages of medicines and/or the medicine regimen.

At an operation 922, alert user when it is time for medication dispensing, doctor's visits, dietary regimens, and/or other medication and care management tasks. In some embodiments, as discussed above operation 922 may include determining a person's distance utilizing proximity sensors for adjusting volume of audio alerts and LED intensity of the visual alert. After repeated attempts, notify through other methods, e.g. phone call until user dispenses medication. If no medication is dispensed by the user (e.g., the user did not push the one touch dispense button on the module 300 to dispense medication or utilize different means to activate the dispense functionality) thus alerting the module that medication has been dispensed) and notify caretaker or others.

At an operation 924, user action or in-action is recorded. Next performing compliance monitoring at an operation 926 and informing caregiver, pharmacy, physicians, health plan and/or other authorized parties of action or inaction. At an operation 928, user dispenses meds. Dispensing meds may require authorization utilizing e.g. pin, passcode, wireless technologies (e.g., RFID, NFC, and the like), optical/proximity sensors, finger/voice print, facial recognition, and/or other biometrics in combination and/or alone. At an operation 930 if user activates dispense feature, pills released to a temporary dispense area while determining whether a cup 307 has been presented and placed in the designated dispensing area at an operation 932. At an operation 934, if the cup 307 is placed in the designated area the pills will be released into the cup 307 and perform compliance/adherence monitoring by informing caregiver, pharmacy, physicians, health plan, payors, insurers, and/or other authorized parties that medicine has been dispensed and released into the cup 307. In some embodiments, if the cup 307 is not placed correctly or not in the designated area (e.g., dispensing area 306), the user will be informed to correct action.

Figure 10B:
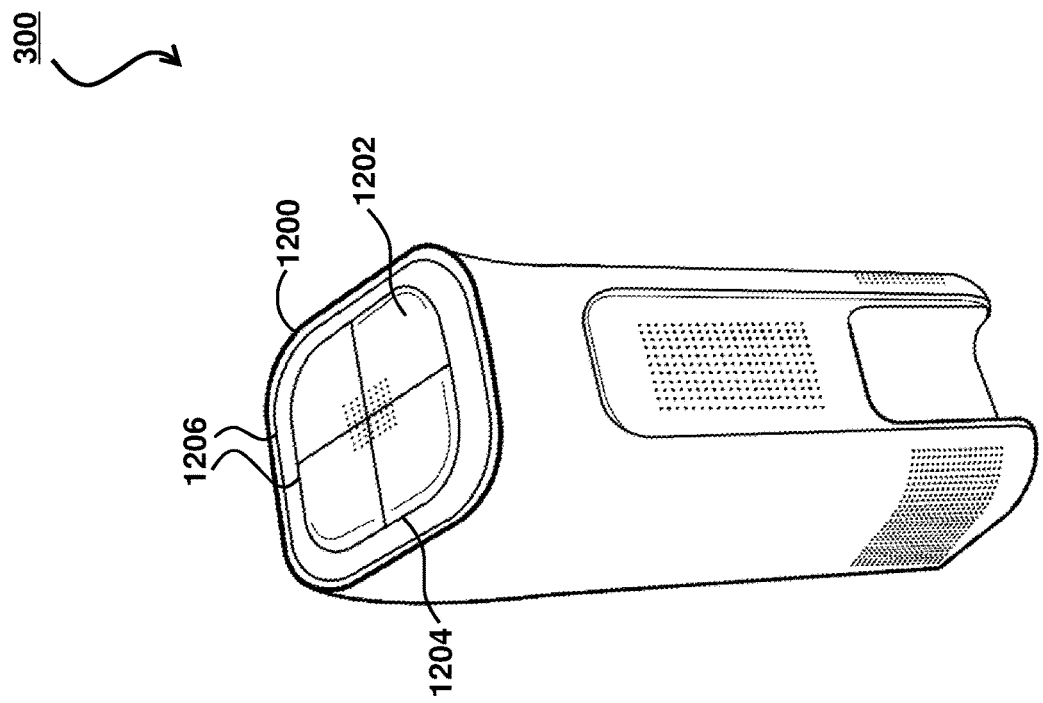
FIGS. 10A-10B depicts a schematic representation of a graphic user interface configured for use with an integrated medication management module in accordance with one or more embodiments.
Figure 10A:
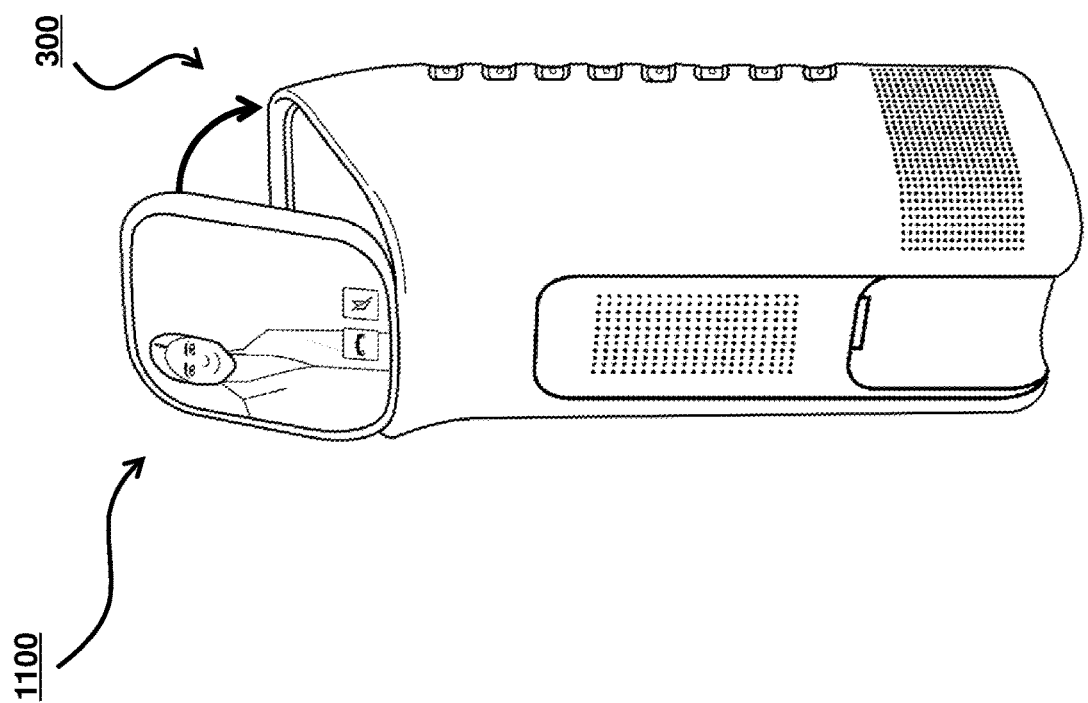

Referring now to FIGS. 10A-10B in conjunction with FIGS. 1-4, FIGS. 10A-10B depicts an exemplary medication management module 300 in accordance with one or more embodiments. As shown in FIG. 10A, in one embodiment, medication management module 300 may include a graphic user interface 1100, similar to that of FIG. 11 discussed in detail below. In this embodiment, GUI 1100 may be rotatably coupled to module 300. By allowing GUI 1100 to rotate and tilt up to be substantially perpendicular, this allows for user-friendliness for patients who may be mobility impaired, and/or visually impaired and may not be able to access GUI 1100 comfortably from a resting position. As shown in FIG. 12B, in one embodiment module 300 may include a GUI 1200. GUI 1200 differs from GUI 1100 and that physical buttons replace touch buttons. The physical buttons may include functionality similar to GUI 1100, which is discussed in detail below. For example physical buttons may include a direct link to a pharmacy 1202, dispense button 1204 may cause dispensing of medication, and/or other functionality 1206, which is discussed in further detail below.

Figure 11:
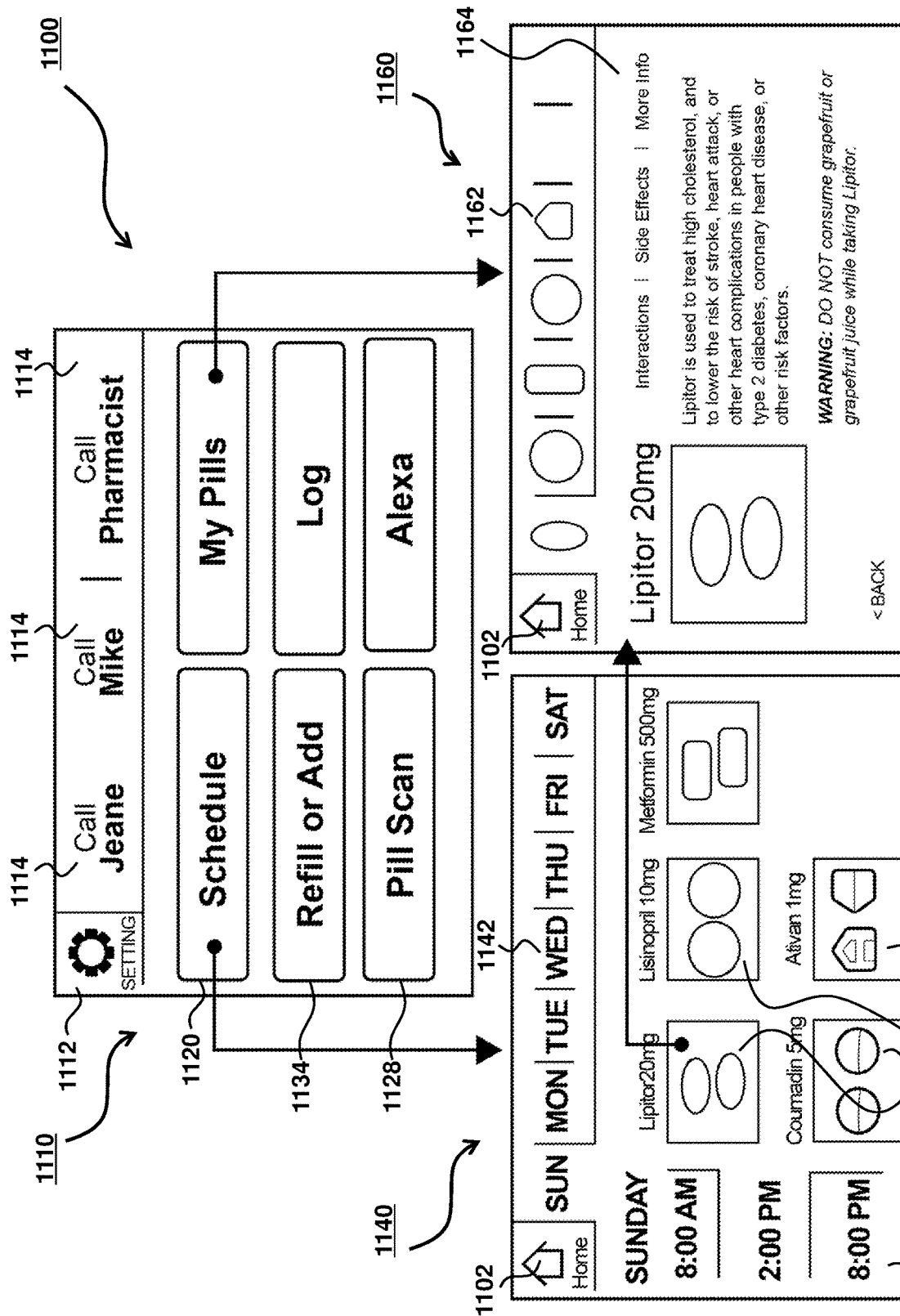
FIG. 11 depicts a schematic representation of a graphic user interface menu configured for use with integrated medication management module in accordance with one or more embodiments.

Referring now to FIG. 11 in conjunction with FIGS. 1-4, FIG. 11 depicts an exemplary graphic user interface in accordance with one or more embodiments. Graphic user interface 1100 may be utilized in connection with medication management module 300. As discussed above, user(s) may be defined as a patient and/or caregiver. Drug(s)/pill(s) may be prescriptions, over the counter drugs, vitamin supplements, and the like. In some embodiments, GUI 1100 may cause displaying of any menu on a user's mobile device (e.g., mobile device 149) and/or computer.

As discussed in further detail below in some embodiments, GUI 1100 may include a display and a selection device. The selection device may include a touch screen functionality of a touchscreen display. GUI 1100 includes one or more processors in communication with memory storing machine readable instructions thereon, the one or more processor configured to execute the machine readable instruction and cause the graphic user interface to retrieve a set of pill options for the menu, each of the pill options representing a medication regimen of a patient. In some embodiments, the GUI 1100 may display the set of pill options of the patient on the display. Upon receiving a menu entry selection signal indicative of the selection device pointing at a selected pill option from the set of pill options, GUI 1100 may, in response to the signal, perform a search of a real time available pharmacist based on the pill option selection. Perform the search may be implemented for example utilizing API pharmacy services 118 C. In some embodiments, GUI 1100 may display a real time video feed on the user interface corresponding to the real time available pharmacist.

In some embodiments, GUI 1100 may display home menu 1110. In one embodiment, home menu 1110 may be associated with functionality that may be displayed on GUI 1100. For example, functionality may include but is not limited to: reviewing and/or adjusting a schedule associated with a medication care plan, ordering a prescription refill or additional medications, scanning a pill in order to determine drug information associated with the pill, reviewing current prescriptions and current pills as part of the medication care plan, accessing adherence history/report, and the compliance events, accessing plug in technology for example, ALEXA™.

As shown in FIG. 11, in some embodiments, home menu 1110 may include scheduling link 1120, refill or add link 1134, scan link 1128, my pills link 1122, log link 1126, and Alexa link 1130. Each link 1120, 1134, 1128, 1122, 1126, and/or 1130 may navigate the user to an additional menu. For example, as shown in FIG. 11, by pressing (e.g., utilizing touchscreen functionality of GUI 1100) scheduling link 1120 the user may be directed to a schedule menu 1140. By pressing my pills link 1122, the user may be directed to a pill/drug information menu 1160.

In some embodiments, utilizing home screen 1110, a user may access user settings via settings link 1112. Accessing setting may allow a user to configure medication management module 300 and customize user preferences. For example preferences may include how many contact links 1114 to include on home screen 1110 and provide for customizing contact links to personal caretakers and healthcare providers and/or emergency response service numbers. For example, a caregiver may add her own name (with or without photo) and phone number or ID of other telephony/VoIP services (e.g., Skype™ and/or Apple™ FaceTime™, "Jeanne", as well as her brother, "Mike", for the speed dial should their elderly parents or love ones want to get a hold of them.

For example, when user/patient press "Call Jean" 1114a or "Call Mike" 1114b (or on the appropriate photo), the medicine medication management module 300 may instantly call or message the phone number specified for Jean or Mike. In this manner a user/patient may communicate with loved ones in addition to accessing pharmacist 1114c when/if needed to inquiry about drug questions or medication care plans. In some embodiments, in addition to voice or video calls, communication may be via text, instant messaging, email, and other electronic methods.

In some embodiments, a user may also access the "Schedule" menu 1120 to confirm or configure the dispensing schedule or see the list of all current medication by accessing "My Pills" 1122. A User may also easily request a refill, schedule refill delivery, and/or add a new prescription, over the counter drugs, and/or vitamins by tapping on the "Refill or Add" link 1134 or see dispensing (missed dosage) history by accessing the "Log" link 1126. In some embodiments, for example by pressing the log link 1126, graphic user interface 1100 may navigate user to an additional menu (not shown) for more details and functionality corresponding to adherence and noncompliance management.

In some embodiments, GUI 1100 may access the functionality of Amazon's voice assistant by pressing Alexa link 1130, or other virtual assistant functionality. Users may also find out more about a pill by pressing the "Pill Scan" and then holding that specific pill in front of the dispenser device 300 (e.g. in front of dispensing area 306 or the display screen 303. In some embodiments, GUI 1100 may display information about that specific drug with image. Information about the specific drug may include but is not limited to: what the drug is used for, benefits of the drug, how the medication should be administered, potential side effects, potential adverse drug interactions, and/or other information corresponding to a particular drug.

In some embodiments, GUI 1100 may cause an audio output (utilizing speakers 228) corresponding to the drug information. For example audio output may audio read aloud information displayed on menus 1110, 1140, 1160 as shown on FIG. 11. In some embodiments, pill scanning may be performed using user's smart device (e.g., mobile device 149). In some embodiments, features and functionality of module 140, 200, 300 may be activated using voice commands (e.g., utilizing speech recognition processor 210) alone and/or in combination with touch and/or physical buttons 220 and GUI 1100.

In some embodiments, upon activation of schedule link 1120, GUI 1100 may display schedule screen 1140 with prepopulated medicine with image 1146, and dosages and proposed scheduled times 1144 based on prescriptions from patient's Doctor(s) and licensed Pharmacist(s) and/or other authorized healthcare professionals and practitioners. User(s) may re-configure the scheduled time 1144 at any time within the confines of the prescription. For example, if the medicine that needs to be taken once daily, user can change the dispensing time from 8 am to 9 am, or to 12 pm—whatever deems best fit to patient's schedule and lifestyle. User may also tap on the day of the week 1142 for scheduling.

For example, one medication may be only needed on every other day or once a week, user could access those day(s) to specify the dispensing time for that particular pill/drug. On this Schedule screen 1140, user may navigate back to the Home Screen 1110 by tapping on the "Home" link 1102 or pressing on image 1146 of any listed drugs could take user to the drug page 1160 with more information about that particular drug Like the Schedule screen 1140, user may navigate to the Home Screen 1110 by tapping on the "Home" icon 1102. If user came to the drug page 1160 from the Schedule screen 1140, user could be taking back to the Schedule screen 1140 when pressed on the "Back" button 1166 or whatever screen user came from such as the Home Screen 1110. In some embodiments, users may also schedule or access on-demand for any of the "as needed" pills (e.g., water pills, painkiller, vitamins, and the like).

In some embodiments, utilizing drug menu 1160, a user may find all the images (with or without the drug name) of their current drugs 1162 or vitamins (whether it's one or five or twelve) shown drug icons on the top or side of the drug menu 1160. A user may press on any of these drugs 1162 (image and/or name) for more information about that particular drug 1164 which may be also read out loud to user based on user preference.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A method for providing integrated medication management of a patient, utilizing a medication management module (140) comprising one or more cartridge slots (310), a pill extractor (504), and one or more processors (142) in communication with a memory (144) having non-transitory machine readable instructions (145) stored thereon that when executed by the one or more processors configure the medication management module to implement the method, the method comprising:
   receiving, by the one or more processors (142), patient data (116) of a patient;
   storing, on the memory, the patient data;
   determining a presence of one or more pill cartridges (400) comprising one or more pills (509), the one or more pills each disposed in a blister pack with a plurality of enclosed pill pockets, each of the plurality of enclosed pill pockets permitting each of the one or more pills to be individually dispensed from the one or more pill cartridges;
   determining, utilizing one or more cartridge slots a cartridge label (402) corresponding to the patient and the one or more pills;
   authenticating the one or more cartridges based on the patient data and the one or more pills;
   determining, in response to authenticating, a medication regimen (920) based on the patient data and the one or more pills;
   extracting, from at least one of the enclosed pill pocket of the blister pack, utilizing the pill extractor, the one or more pills from the one or more pill cartridges by releasing the pill out from its enclosed pill pocket; and
   dispensing the one or more pills at a predetermined time in a predetermined amount based on the medication regimen.

2. The method of claim 1, the method further comprising:
   verifying, prior to dispensing the one or more pills, a correct extraction of the one or more pills.

3. The method of claim 1, the method further comprising verifying a correct dispensing of the one or more pills at the predetermined time in the predetermined amount.

4. The method of claim 3, the method further comprising verifying the correct extraction of the one or more pills utilizing one or more optic sensors (222) and/or cameras (234) to verify the correct extraction of the one or more pills.

5. The method of claim 1, where dispensing the one or more pills comprises utilizing a vibration motor (236).

6. The method of claim 1, wherein authenticating the one or more cartridges based on the patient data and the one or more pills comprises determining real-time adjustments to the medication regimen.

7. The method of claim 1, wherein dispensing the one or more pills comprises issuing an alert, the alert comprising at least one of an audio alert, a visual alert, and/or a vibration alert.

8. The method of claim 7, wherein issuing the alert comprises utilizing proximity sensors to adjust at least one of a volume, an intensity level, or a duration of the alert.

9. The method of claim 1, wherein dispensing comprises utilizing a 1-touch button or a biometric authentication.

10. The method of claim 1, wherein the one or more cartridge slots are configured for error proof insertion of the one or more cartridges.

11. The method of claim 1, wherein dispensing the one or more pills comprises dispensing the one or more pills into a holding compartment, wherein the one or more pills are verified with patient data and the medication regimen to ensure error-proof pill administration.

12. A medication management module configured for providing integrated medication and care management, the medication management module comprising:
  one or more cartridge slots configured to receive a pill cartridge comprising one or more pills;
  an extractor mechanism comprising a pill extractor; and
  one or more processors in communication with memory storing machine readable instructions thereon, the one or more processor configured to execute the machine readable instruction and cause the apparatus to:
  receiving, by the one or more processors (142), patient data (116) of a patient;
  storing, on the memory, the patient data,
  determining a presence of one or more pill cartridges (400) comprising one or more pills (509), the one or more pills each disposed in a blister pack with a plurality of enclosed pill pockets, each of the plurality of enclosed pill pockets permitting each of the one or more pills to be individually dispensed from the one or more pill cartridges;
  determining, utilizing one or more cartridge slots; a cartridge label (402) corresponding to the patient and the one or more pills;
  authenticating the one or more cartridges based on the patient data and the one or more pills;
  determining, in response to authenticating, a medication regimen (920) based on the patient data and the one or more pills;
  extracting, from at least one of the enclosed pill pocket of the blister pack, utilizing the pill extractor, the one or more pills from the one or more pill cartridges by releasing the pill out from its enclosed pill pocket;
  verifying a correct extraction of the one or more pills;
  dispensing the one or more pills at a predetermined time in a predetermined amount based on the medication regimen; and
  verifying a correct dispensing of the one or more pills at the predetermined time in the predetermined amount.

13. The apparatus of claim 12, wherein verifying the correct extraction of the one or more pills comprises utilizing one or more optic sensors (222) and/or cameras (234) to verify the correct extraction of the one or more pills.

14. The apparatus of claim 12, where dispensing the one or more pills comprises utilizing a vibration motor (236).

15. The apparatus of claim 12, wherein authenticating the one or more cartridges based on the patient data and the one or more pills comprises determining real-time adjustments to the medication regimen.

16. The apparatus of claim 12, wherein dispensing the one or more pills comprises issuing an alert, the alert comprising at least one of an audio alert, a visual alert, and/or a vibration alert.

17. The apparatus of claim 16, wherein issuing the alert comprises utilizing proximity sensors to adjust at least one of a volume, an intensity level, or a duration of the alert.

18. The apparatus of claim 12, wherein dispensing comprises utilizing a 1-touch button or a biometric authentication.

19. The apparatus of claim 12, wherein the one or more cartridge slots are configured for error proof insertion of the one or more cartridges.

20. The apparatus of claim 12, wherein dispensing the one or more pills comprises dispensing the one or more pills into a holding compartment, wherein the one or more pills are verified with patient data and the medication regimen to ensure error-proof pill administration.

* * * * *